US009290464B2

(12) United States Patent
Park et al.

(10) Patent No.: US 9,290,464 B2
(45) Date of Patent: *Mar. 22, 2016

(54) PHARMACEUTICAL COMPOSITION FOR INHIBITING APOPTOSIS OF NEURON OR NEURODEGENERATION

(71) Applicant: SK BIOPHARMACEUTICALS CO., LTD., Seoul (KR)

(72) Inventors: Cheol Hyoung Park, Daejeon (KR); Hye Kyung Min, Daejeon (KR); In Suk Park, Daejeon (KR); Mi Jung Lim, Daejeon (KR); Ji Won Lee, Daejeon (KR); Jin Yong Chung, Daejeon (KR); Yeo Jin Yoon, Daejeon (KR); Joo Young Park, Daejeon (KR)

(73) Assignee: SK BIOPHARMACEUTICALS CO., LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/337,628

(22) Filed: Jul. 22, 2014

(65) Prior Publication Data

US 2014/0350062 A1    Nov. 27, 2014

Related U.S. Application Data

(63) Continuation of application No. 13/695,809, filed as application No. PCT/KR2011/003318 on May 3, 2011, now Pat. No. 8,841,335.

(30) Foreign Application Priority Data

May 3, 2010    (KR) .................. 10-2010-0041436

(51) Int. Cl.
    *A61K 31/42*    (2006.01)
    *A61K 31/425*    (2006.01)
    *A61K 31/41*    (2006.01)
    *C07D 261/08*    (2006.01)
    *A61K 31/4196*    (2006.01)
    *A61K 31/4245*    (2006.01)
    *A61K 31/433*    (2006.01)

(52) U.S. Cl.
    CPC .......... *C07D 261/08* (2013.01); *A61K 31/4196* (2013.01); *A61K 31/4245* (2013.01); *A61K 31/433* (2013.01)

(58) Field of Classification Search
None
See application file for complete search history.

(56) References Cited

U.S. PATENT DOCUMENTS

| 8,044,208 B2 | 10/2011 | Kallus et al. ............... 564/272.1 |
| 8,153,795 B2 | 4/2012 | Sundermann et al. .......... 546/19 |

FOREIGN PATENT DOCUMENTS

| DE | 102005030051 A1 | 12/2006 | ........... C07D 498/10 |
| DE | 102005049385 A1 | 4/2007 | ........... C07D 413/14 |
| EP | 2269990 | 1/2011 | ........... C07D 209/34 |
| WO | 03/078394 | 9/2003 | ........... C07D 473/06 |
| WO | 2006/042245 | 4/2006 | ........... C07D 261/08 |
| WO | 2007/017261 | 2/2007 | ........... C07D 473/06 |
| WO | 2007/022182 | 2/2007 | ........... A61K 31/428 |
| WO | 2007/150025 | 12/2007 | |
| WO | 2008/074384 | 6/2008 | ............. A61K 31/41 |
| WO | 2008/076356 | 6/2008 | ............. A01N 43/82 |
| WO | 2010/001365 | 1/2010 | ......... A61K 31/4196 |
| WO | 2010/039947 | 4/2010 | ........... C07D 211/76 |
| WO | 2010/098600 | 9/2010 | ........... C07D 249/10 |

OTHER PUBLICATIONS

Kimura et al. Stem Cells 25 (2007) 115-124.*
Gfesser, et al. (2004) "Structure-activity relationships of non-imidazole $H_3$ receptor ligands. Part 3: 5-Substituted 3-phenyl-1,2,4-oxadiazoles as potent antagonists." *Bioorganic & Medicinal Chemistry Letters*, 14:673-676.
Akerud, et al., "Neuroprotection through Delivery of Glial Cell Line-Derived Neurotrophic Factor by Neural Stem Cells in a Mouse Model of Parkinson's Disease.", The Journal of Neuroscience, 21:8108-8118, 2001.
Alberch, et al., "Neuroprotection by neurotrophins and GDNF family members in the excitotoxic model of Huntington's Disease." Brain Research Bulletin, 57:817-822, 2002.
Armentero, et al. "Dopamine Receptor Agonists Mediate Neuroprotection in Malonate-Induced Striatal Lesion in the Rat." Experimental Neurology, 178:301-305.
Beal, et al. "Age-Dependent Striatal Excitotoxic Lesions Produced by the Endogenous Mitochondrial Inhibitor Malonate." J. Neurochem. 61:1147-1150, 1993.
Beal, et al., Neuroprotective and Neurorestorative Strategies for Neuronal Injury., Neurotoxicity Research, 2:71-84, 2000.
Beal, "Mitochondria Take Center Stage in Aging and Neurodegeneration.", Ann. Neurol., 58:495-505, 2005.
Beal, "Mitochondrial dysfunction in neurodegenerative diseases and stroke: Neuroprotective strategies.", Journal of Neurological Sciences, 283:240-320, 2009.
Behl, et al., "Serial Review: Causes and Consequences of Oxidative Stress in Alzheimer's Disease." Free radical Biology & Medicine, 33(2): 182-191, 2002.
Berger, et al., "Retrograde Degeneration of Nitrostriatal Neurons Induced by Instrastriatal 6-Hydroxydopamine Injection in Rats.", Brain Res., 26:301-307, 1991.
Burlacu, "Regulation of apoptosis by Bcl-2 family proteins." J. Cell Mol. Med., 7:249-257, 2003.

(Continued)

*Primary Examiner* — Jeffrey S Lundgren
*Assistant Examiner* — Michael Schmitt
(74) *Attorney, Agent, or Firm* — Harness, Dickey & Pierce, P.L.C.

(57) ABSTRACT

Provided is a pharmaceutical composition for inhibiting apoptosis of neurons or neurodegeneration. The pharmaceutical composition effectively prevents or treats diseases related to apoptosis of neurons or neurodegeneration.

3 Claims, 24 Drawing Sheets

(56) References Cited

OTHER PUBLICATIONS

Canu, et al, "In vitro cultured neurons for molecular studies correlating apoptosis with events related to Alzheimer disease.", Cerebellum, 2:270-278, 2003.

Cassarino, et al., "An evaluation of the role of mitochondria in neurodegenerative diseases: mitochondrial mutations and oxidative pathology, protective nuclear responses, and cell death in neurodegeneration.", Brain Res Review, 29(1):1-25, 1999.

Chen, et al., "Neuroprotection by Caffeine and A2A Adenosine Receptor Inactivation in a model of Parkinson's Disease.", J. Neurosci., 21:RC143, 2001.

Friedlander, "Apoptosis and Caspases in Neurodegenerative Diseases.", The New England Journal of Medicine, 348(14):1365-1375, 2003.

Gerlach, et al., "Animal models of Parkinson's Disease: an empirical comparison with the phenomenology of the disease in man.", J. Neural Trasm., 103:987-1041.

Gorman, "Neuronal cell death in neurodegenerative diseases: recurring themes around protein handling.", Journal of Cellular and Molecular Medicine, 12:2263-2280, 2008.

Gross, et al., "BCL-2 family members and the mitochondria in apoptosis." Genes and Development, 13:1899-1911, 1999.

Kroemer, "Mitochondrial control of apoptosis: an introduction." Biochem Biophys Res Commun., 304(3):433-435, 2003.

Lee, et al., "Dopaminergic Neuronal Degeneration and Motor Impairments Following Axon Terminal Lesion by Intrastriatal 6-Hydroxydopamine in the Rat.", Neurosci., 72:641-653, 1996.

Lin, et al., "Neuroprotection by Small Molecule Activators of the Nerve Growth Factor Receptor.", The Journal of Pharmacology and Experimental Therapeutics, 322:59-69, 2007.

Lotharius, et al., "Distinct Mechanisms Underlie Neurotoxin-Mediated Cell Death in Cultured Dopaminergic Neurons.", J. Neurosci., 19:1284-1293, 1999.

Maruyama, et al., "Neuroprotection by propargylamines in Parkinson's disease Suppression of apoptosis and induction of prosurvival genes.", Neurotoxicology and Teratolgy, 24:675-682, 2002.

Mattson, "Apoptosis in Neurodegenerative Disorders." Nature Reviews Molecular Cell Biology, 1:120-130, 2000.

Mattson, et al., "Ageing and neuronal vulnerability." Nat. Rev. Neurosci., 7:278-294, 2006.

Monopoli, et al., "Blockade of adenosine A2A receptors by SCH 58261 results in neuroprotective effects in cerebral ischaemia in rats.", Neuro Report, 9:3955-3959, 1998.

Nagahara, et al., "Neuroprotective effects of brain-deprived neurotrophic factor in rodent and primate models of Alzheimer's Disease.", Narure medicine.

Pettmann, et al., "Neruonal Cell Death" Neuron., 20:633-647, 1998.

Przedborski, et al., "Dose-Dependent Lesions of the Dopaminergic Nigrostriatal Pathway Induced by Intrastriatal Injection of 6-Hydroxydopamine.", Neurosci., 67:631-647, 1995.

Przedborski, et al., "Mechanisms of MPTP Toxicity.", Mov. Disord., 13:35-38, 1998.

Przedborski, et al., "The parkinsonian toxin MPTP: action and mechanism." Restor. Neurol. Neurosci., 16:135-142, 2000.

Sauer, et al., "Progressive Degeneration of Nigrostriatal Dopamine Neurons Following Instrstriatal Terminal Lesions with 6-Hydroxydopamine: A Combined Retrograde Tracing and Immunocytochemical Study in the Rat.", Neurosci., 59:401-415, 1994.

Soane, et al., "Inhibition of Mitochondrial Neural Cell Death Pathways by Protein Transduction of Bcl-2 Family Proteins.", Journal of Bioenergetics and Biomembranes, 37:179-190, 2005.

Sonsalla, et al. "Inhibition of striatal energy metabolism produces cell loss in the ipsilateral substantia nigra.", Brain Res., 773:223-226, 1997.

Speciale, "MPTP Insights into parkinsonian neurodegeneration." Neurotoxicol. Teratol. 24:607-620, 2002.

Tipton, et al., "Advances in Our Understanding of the Mechanisms of the Neurotoxicity of MPTP and Related Compounds.", J. Neurochem., 61:1191-1206, 1993.

Velikorodov, et al., "Synthesis and Cardiovascular Activity of Some Azaheterocycles with Carbamate Groups.", Pharmaceutical Chemistry Journal, vol. 40, No. 4, 182-185, 2006.

Wu, et al., "Treatment of Parkinson's' Disease What's on the Horizon?", CNS Drugs, 19:723, 2005.

Youdim, et al., "The therapeutic potential of monoamine oxidase inhibitors." Nat. Rev. Neurosci., 7:295-309, 2006.

Yuan, et al., "Diversity in the Mechanisms of Neuronal Cell Death." Neuron, 40:401-413, 2003.

Zeevalk, et al., "Oxidative Stress During Energy Impairment in Mesencephalic Cultures is not a Downstream Consequence of a Secondary Excitotoxicity.", Neuroscience, 96:309-316, 2000.

Zhang, et al., "Neuroprotective effects of huperzine A: new therapeutic targets for neurodegenerative disease." TRENDS in Pharmaceutical Sciences, 27:619-625, 2006.

PCT/KR2011/003318 International Search Report dated Jan. 10, 2012 (3 pgs.).

The extended European Search Report issued in EP 11777560.1, dated Feb. 13, 2014.

\* cited by examiner

PHARMACEUTICAL COMPOSITION FOR INHIBITING APOPTOSIS OF NEURON OR NEURODEGENERATION

CROSS-REFERENCE TO RELATED APPLICATIONS

This is a continuation application of U.S. application Ser. No. 13/695,809 filed on Nov. 2, 2012 which is a national phase application of International Application No. PCT/KR2011/003318 filed on May 3, 2011 which claims the benefit and priority to Korean Patent Application No. 10-2010-0041436 filed on May 3, 2010. The entire disclosures of the applications identified in this paragraph are incorporated herein by references.

TECHNICAL FIELD

This application claims the benefit of Korean Patent Application No. 10-2010-0041436, filed on May 3, 2010, in the Korean Intellectual Property Office, the disclosure of which is incorporated herein in its entirety by reference.

The present invention relates to a pharmaceutical composition for inhibiting apoptosis of neurons or neurodegeneration.

BACKGROUND ART

Apoptosis of neurons may be induced in normal physiological functions such as the Neural development or in pathological processes such as diseases. During the developmental process of neurons, excess neurons are removed through apoptosis in order for optimal, precise connection between presynapse and postsynapse (Neuron, 40:401-413 (2003); Neuron, 20:633-647 (1998)). A wide range of apoptosis of neurons is observed in neurodegenerative diseases such as amyotrophic lateral sclerosis, Alzheimer's disease and Parkinson's disease, a stroke and external injuries. The direct cause of these diseases has not been found yet, however, this is associated with apoptosis and the apoptosis is affected by various factors such as oxidative stress, dysregulation of calcium homeostasis, dysfunction of mitochondria, an increase in the generation of reactive oxygen species, excitotoxicity, caspase activation, and trophic deprivation (Nature Reviews Molecular Cell Biology, 1:120-130 (2000), Neurotoxicology and Teratology, 24:675-682 (2002)).

In the case of Parkinson's disease, it is reported that the dysfunction of mitochondria increases the secretion of calcium and the generation of reactive oxygen species, thereby inducing oxidative stress to decrease the activity of antioxidative systems. In addition, there is a report about association between excitotoxicity by glutamate and Parkinson's disease (Neurotoxicology and Teratology, 24:675-682 (2002)).

In the case of Alzheimer's disease, it is reported that the apoptosis of neurons is associated with oxidative stress, dysregulation of ion homeostasis, growth factor deprivation, accumulation of amyloid A$\beta$, metabolic impairment, dysfunction of mitochondria, DNA damage, and protein aggregation (Nat. Rev. Neurosci., 7:278-294 (2006); Cerebellum, 2:270-278 (2003)).

Currently, various types of neuroprotective agents used for protecting neurons from apoptosis induced by various mechanisms are proposed (Neurotoxicology and Teratology, 24:675-682 (2002)). Examples of the neuroprotective agents include antioxidants, ion chealators, free radical scavengers, neurotrophic factors, excitatory amino acid antagonists, bioenergic supplements, immunosuppressants, and formulations preventing aggregation or accumulation of protein. However, medicines that effectively inhibit apoptosis of neurons or neurodegeneration are not commercially available yet, and thus there is still a need to develop a pharmaceutical composition for inhibiting apoptosis of neurons or neurodegeneration.

DISCLOSURE OF INVENTION

Technical Problem

The present invention provides a pharmaceutical composition for inhibiting apoptosis of neurons or neurodegeneration.

The present invention also provides a pharmaceutical composition for neuroprotection or neurorestoration.

Additional aspects will be set forth in part in the description which follows and, in part, will be apparent from the description, or may be learned by practice of the presented embodiments.

Solution to Problem

The present invention will now be described in detail with reference to the accompanying drawings.

The present invention provides a pharmaceutical composition for inhibiting apoptosis of a neuron or neurodegeneration including a therapeutically effective amount of a compound selected from the group consisting of a substituted azole derivative represented by Formula I below, pharmaceutically acceptable salts thereof, isomers of the substituted azole derivative, solvates of the substituted azole derivative, and combinations thereof; and a pharmaceutically acceptable carrier.

The present invention also provides a pharmaceutical composition for neuroprotection including a therapeutically effective amount of a compound selected from the group consisting of a substituted azole derivative represented by Formula I below, pharmaceutically acceptable salts thereof, isomers of the substituted azole derivative, solvates of the substituted azole derivative, and combinations thereof; and a pharmaceutically acceptable carrier.

The present invention also provides a pharmaceutical composition for neurorestoration including a therapeutically effective amount of a compound selected from the group consisting of a substituted azole derivative represented by Formula I below, pharmaceutically acceptable salts thereof, isomers of the substituted azole derivative, solvates of the substituted azole derivative, and combinations thereof; and a pharmaceutically acceptable carrier.

The present invention also provides a pharmaceutical composition for prevention or treatment of neurodegenerative diseases or ischemia- or repurfusion-related disease, the composition including a therapeutically effective amount of a compound selected from the group consisting of a substituted azole derivative represented by Formula I below, pharmaceutically acceptable salts thereof, isomers of the substituted azole derivative, solvates of the substituted azole derivative, and combinations thereof; and a pharmaceutically acceptable carrier.

The present invention also provides a pharmaceutical composition for prevention or treatment of diseases selected from the group consisting of a stroke, Alzheimer's disease, Huntington's disease, Parkinson's disease, Pick's disease, Creutzfeld-Jacob's disease, Parkinson-ALS-dementia complex, Wilson's disease, multiple sclerosis, progressive supranuclear palsy, neuropathic pain-related bipolar disorders, corticobasal degeneration, schizophrenia, attention deficit hyperactivity disorder (ADHD), dementia, amyotrophic lateral sclerosis, retinal disease, epilepsy, apoplexy, transient ischemic attacks, myocardial ischemia, muscle ischemia, ischemia caused by surgical techniques regarding extended suspension of blood flow to brain, a head injury, a spinal cord injury, hypoxia, and depression, the composition including a therapeutically effective amount of a compound selected from the group consisting of a substituted azole derivative represented by Formula I below, pharmaceutically acceptable salts thereof, isomers of the substituted azole derivative, solvates of the substituted azole derivative, and combinations thereof; and a pharmaceutically acceptable carrier:

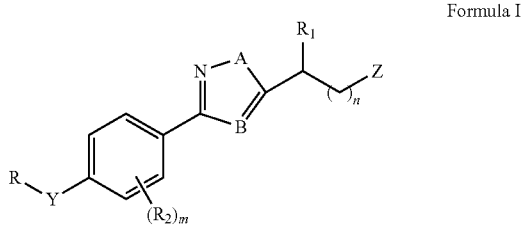

Formula I wherein R is selected from the group consisting of a substituted or unsubstituted $C_1$-$C_{15}$ arylalkyl group, a substituted or unsubstituted $C_1$-$C_{10}$ heteroarylalkyl group, and a substituted or unsubstituted, linear, branched or cyclic $C_1$-$C_{10}$ alkyl group;

Y is selected from the group consisting of O and —N—$R_1$;

$R_1$ is at least one selected from the group consisting of H and a linear or branched $C_1$-$C_3$ alkyl group;

$R_2$ is selected from the group consisting of H and halogen;

A is selected from the group consisting of N, O, and S;

B is C or N;

Z is selected from the group consisting of a substituted or unsubstituted heterocyclic group, carbamate, —OC(=O)NR$_3$R$_4$, NH$_2$, NR$_5$R$_6$, NC(=NH)NH$_2$, and —NC(=O)NH$_2$;

each of $R_3$ and $R_4$ is independently selected from the group consisting of H; $C_1$-$C_5$ alkyl unsubstituted or substituted by at least one selected from the group consisting of NH$_2$, and NR$_7$R$_8$; heterocyclic ring unsubstituted or substituted by $C_1$-$C_3$ alkyl; or $R_3$ and $R_4$ together may form a 5- or 7-membered heterocyclic ring unsubstituted or substituted by $C_1$-$C_3$ alkyl;

each of $R_5$ and $R_6$ is independently selected from the group consisting of H; $C_2$-$C_3$ alkene; $C_2$-$C_3$ alkyne; and linear or branched $C_1$-$C_7$ alkyl unsubstituted or substituted by at least one selected from the group consisting of —OH, —C(O)NH$_2$, $C_1$-$C_3$ alkoxy, and carbamate, or $R_5$ and $R_6$ together may form a substituted or unsubstituted aliphatic cyclicamine or aromatic cyclicamine;

each of $R_7$ and $R_8$ is independently at least one selected from the group consisting of H and a linear or branched $C_1$-$C_3$ alkyl group;

m is an integer in the range of 0 to 4; and n is an integer in the range of 0 to 5.

The pharmaceutical composition may include a therapeutically effective amount of a compound selected from the group consisting of a substituted azole derivative represented of Formula I, pharmaceutically acceptable salts thereof, isomers of the substituted azole derivative, solvates of the substituted azole derivative, and combinations thereof.

The term "treatment" used herein should be interpreted to include, in animals that have never been diagnosed to have diseases, disorders or conditions caused by apoptosis of neurons or neurodegeneration, but are at high risk of developing such diseases, disorders or conditions, prevention of development of the diseases, disorders or conditions, inhibition of the diseases, disorders or conditions, that is, inhibition of development of the diseases, disorders or conditions and alleviation of the diseases, disorders or conditions, that is, causation of degeneration of the diseases, disorders or conditions. Therefore, the term "therapeutically effective amount" used herein refers to a sufficient amount used in achieving the pharmacological effects described above.

The substituted azole derivative of Formula I may be prepared using known compounds or compounds that may be easily prepared therefrom by those of ordinary skills regarding the field of compound synthesis in the art to which the present invention pertains. Therefore, a preparation method of the substituted azole derivative of Formula I, which will be described later, is an exemplary embodiment for illustrative purposes only and the order of unit operations may be selectively changed, if necessary, not intended to limit the scope of the invention.

Scheme 1: Synthesis of azole

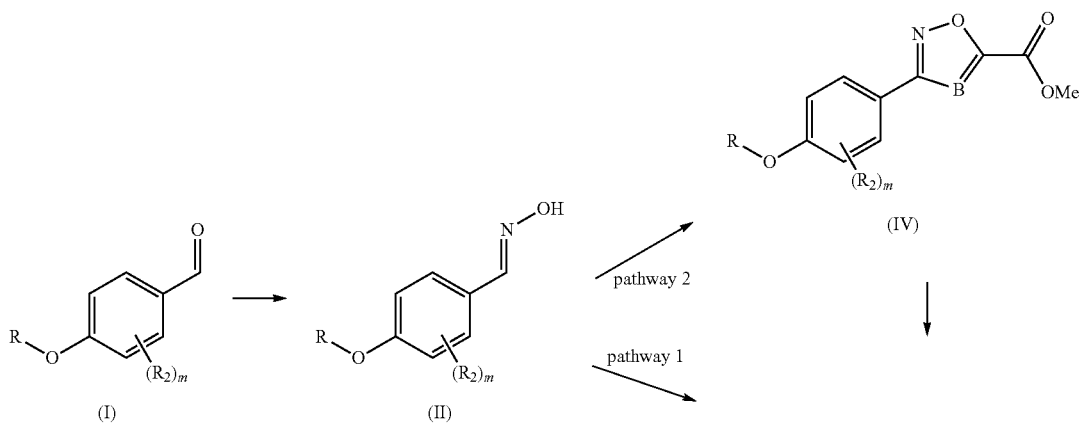

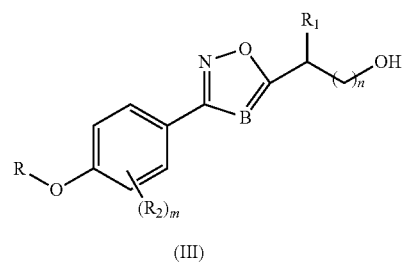

(III)

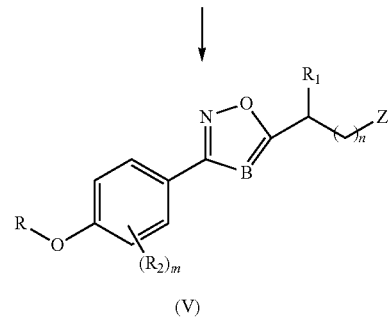

(V)

R may be a benzyl group, and R₂, Z, B, m, and n are the same as defined above. A general synthesis method of azole may be performed in such a manner that oxime (II) is prepared from aldehyde (I) as a starting material, the prepared oxime compound is subjected to [3+2] cycloaddition with alkynes or nitriles in the presence of NaOCl to obtain an azole compound (III or IV), and desired functional groups are then introduced into the azole compound to obtain a final compound (V).

Scheme 2: Synthesis of thiazole

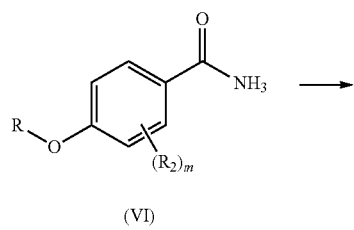

(VI)

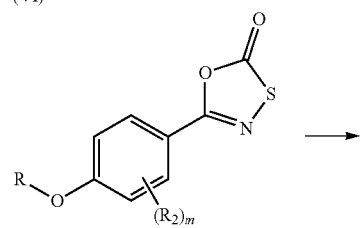

(VII)

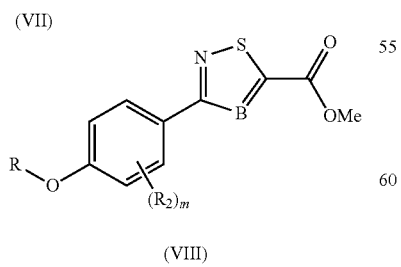

(VIII)

-continued

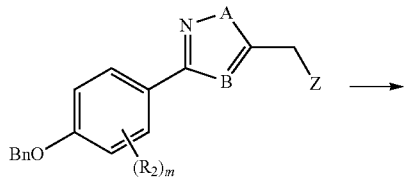

(X)                    (IX)

R may be a benzyl group, and R₂, Z, B, and m are the same as defined above. A general synthesis method of thiazole may be performed in such a manner that oxathiazolon (VII) is prepared from amide (VI) as a starting material, the prepared compound is subjected to [3+2] cycloaddition with alkynes or nitrites in the presence of NaOCl to obtain a thiazole compound (VIII), and the thiazole compound is reduced (IX) and desired functional groups are introduced thereinto to obtain a final compound (X).

Scheme 3

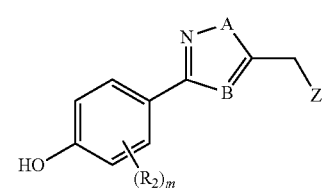

(XI)

(XII)

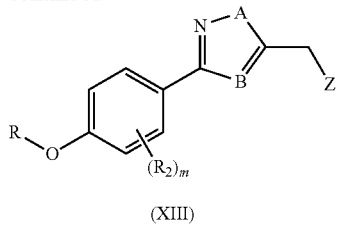

(XIII)

R, R$_2$, Z, A, m, and B are the same as defined above. A general synthesis method of a final compound (XIII) may be performed in such a manner that a hydroxyphenyl derivative (XII) is prepared by debenzylation reaction of a compound (XI) as a starting material, and desired functional groups are introduced thereinto to obtain the final compound (XIII).

Scheme 4

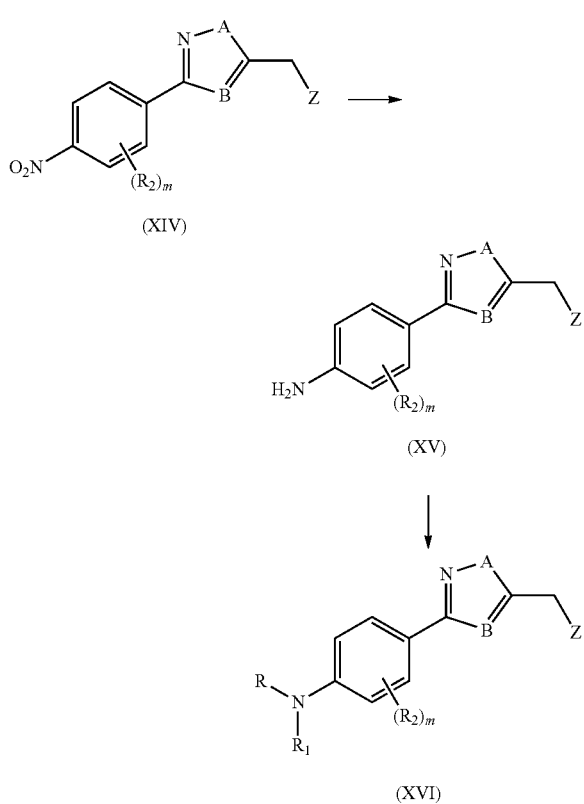

R, R$_1$, R$_2$, Z, A, m, and B are the same as defined above. A general synthesis method of a final compound (XVI) may be performed in such a manner that an aminophenyl derivative (XV) is synthesized by reduction of a nitrophenyl derivative (XIV) as a starting material, and the synthesized compound is then subjected to reductive amination with desired aldehyde to obtain the final compound (XVI).

The azole derivative includes, in addition to the azole derivative of Formula I, pharmaceutically acceptable salts thereof, that is, additional salts of acid or base, and stereochemical isomers thereof, and the salts may be any salt that maintains the activity of a parent compound in the subjects administered therewith without undesirable effects. Such salts may be inorganic or organic salts. Examples of the salts include acetic acid, nitric acid, aspartic acid, sulfonic acid, sulfuric acid, maleic acid, glutamic acid, formic acid, succinic acid, phosphoric acid, phthalic acid, tannic acid, tartaric acid, hydrobromic acid, propionic acid, benzenesulfonic acid, benzoic acid, stearic acid, esilate, lactic acid, bicarbonic acid, bisulfuric acid, bitartaric acid, oxalic acid, butyric acid, calcium edetate, camsylic acid, carbonic acid, chlorobenzoic acid, citric acid, edetic acid, toluenesulfonic acid, edisylic acid, esylic acid, fumaric acid, gluceptic acid, pamoate, gluconic acid, glycollylarsanilic acid, methylnitric acid, polygalactronic acid, hexylresorcinoic acid, malonic acid, hydrabamic acid, hydrochloric acid, hydroiodic acid, hydroxynaphthoic acid, isethionic acid, lactobionic acid, mandelic acid, estolic acid, mucic acid, napsylic acid, muconic acid, p-nitromethanesulfonic acid, hexamic acid, pantothenic acid, monohyrogen phosphoric acid, dihyrogen phosphoric acid, salicylic acid, sulfamic acid, sulfanilic acid, methanesulfonic acid, and teoclic acid. Also, the form of basic salt may include, for example, ammonium salt, alkali metal salts and alkaline earth metal salts such as lithium, sodium, potassium, magnesium and calcium salts, organic base salts such as benzathine, N-methyl-D-glucamine and hydrabamine salts, and salts having amino acids such as arginine and lysine. Meanwhile, the form of salts may be converted to free forms by treatment with suitable bases or acids. The term "additional salt" used herein means salts that includes solvates which the substituted azole derivative of Formula I or salts thereof can form. The solvates may be hydrates or alcoholates.

As used herein, the term "stereochemical isomers of the substituted azole derivative of Formula I" refers to all possible forms that the substituted azole derivative of Formula I may have. Unless specified or mentioned otherwise, the chemical names of the substituted azole derivative of Formula I indicate mixtures of all possible stereochemical isomers, including all diastereomers and enantiomers of basic molecular structures. Particularly, each chiral center may have either R- or S-configuration, and substituents on bivalent cyclic (partially) saturated radicals may have a cis- or transconfiguration. Compounds having double bonds may have E- or Z-stereochemistry. All stereochemical isomers of the substituted azole derivative of Formula I are intended to be included within the scope of the present invention.

According to the definition of Formula I above, examples of the substituted azole derivatives may include carbamic acid 3-(4-benzyloxy-phenyl)-isoxazole-5-yl methyl ester, carbamic acid 3-(4-benzyloxy-phenyl)-[1,2,4]oxadiazole-5-yl methyl ester, carbamic acid 3-(4-benzyloxy-phenyl)-isothiazole-5-yl methyl ester, carbamic acid 3-(4-benzyloxy-phenyl)-[1,2,4]thiadiazole-5-yl methyl ester, carbamic acid 3-(4-benzyloxy-2-chloro-phenyl)-isoxazole-5-yl methyl ester, carbamic acid 3-(4-benzyloxy-3-chloro-phenyl)-isoxazole-5-yl methyl ester, carbamic acid 3-(4-benzyloxy-3-bromo-phenyl)-isoxazole-5-yl methyl ester, carbamic acid 3-(4-benzyloxy-3-fluoro-phenyl)-isoxazole-5-yl methyl ester, carbamic acid 3-(4-benzyloxy-3,5-dimethyl-phenyl)-isoxazole-5-yl methyl ester, carbamic acid 3-[4-(1-phenyl-ethoxy)-phenyl]-isoxazole-5-yl methyl ester, carbamic acid 3-[4-(2-fluoro-benzyloxy)-phenyl]-isoxazole-5-yl methyl ester, carbamic acid 3-[4-(3-fluoro-benzyloxy)-phenyl]-isoxazole-5-yl methyl ester, carbamic acid 3-[4-(4-fluoro-benzyloxy)-phenyl]-isoxazole-5-yl methyl ester, carbamic acid 3-[4-(2,6-difluoro-benzyloxy)-phenyl]-isoxazole-5-yl methyl ester, carbamic acid 3-[4-(2,3-difluoro-benzyloxy)-phenyl]-isoxazole-5-yl methyl ester, carbamic acid 3-[4-(3,5-difluoro-benzyloxy)-phenyl]-isoxazole-5-yl methyl ester, carbamic acid 3-[4-(3,4-difluoro-benzyloxy)-phenyl]-isoxazole-5-yl methyl ester, carbamic acid 3-[4-(2,4,6-trifluorobenzyloxy)-phenyl]-isoxazole-5-yl methyl ester, carbamic acid 3-[4-(3-trifluoromethyl-benzyloxy)-phenyl]-isoxazole-5-yl methyl ester, carbamic acid 3-[4-(3-chloro-benzyloxy)-phenyl]-isoxazole-5-yl methyl ester, carbamic acid 3-[4-(2-chloro-benzyloxy)-phenyl]-isoxazole-5-yl methyl ester, carbamic acid 3-[4-(4-chloro-benzyloxy)-phenyl]-isoxazole-5-yl methyl ester, carbamic acid 3-[4-(2,6-dichloro-benzyloxy)-phenyl]-isoxazole-5-yl methyl ester, carbamic acid 3-[4-(2,5-dichloro-benzyloxy)-phenyl]-isoxazole-5-yl methyl ester, carbamic acid 3-[4-(2-chloro-5-fluoro-benzyloxy)-phenyl]-isoxazole-5-yl methyl ester, carbamic acid 3-[4-(3-nitro-benzyloxy)-phenyl]-isoxazole-5-yl methyl ester, 4-[4-(5-carbamoyloxymethyl-isoxazole-3-yl)-phenoxymethyl]-benzoic acid methyl ester, carbamic acid 3-[4-(4-methyl-benzyloxy)-phenyl]-isoxazole-5-yl methyl ester, carbamic acid 3-[4-(2-methyl-benzyloxy)-phenyl]-isoxazole-5-yl methyl ester, carbamic acid 3-[4-(3-methoxy-benzyloxy)-phenyl]-isoxazole-5-yl methyl ester, 3-[4-(3-trifluoromethyl-benzyloxy)-phenyl]-isoxazole-5-yl methyl ester, carbamic acid 3-[4-(4-isopropyl-benzyloxy)-phenyl]-isoxazole-5-yl methyl ester, and carbamic acid 3-[4-(4-tert-butyl-benzyloxy)-phenyl]-isoxazole-5-yl methyl ester. Preparation methods of these azole derivatives are disclosed in Korean Patent Application No. 2009-15856 filed by the inventors of the present application, and the disclosure of which is incorporated herein in its entirety by reference.

According to an embodiment of the present invention, the substituted azole derivative of Formula I may be carbamic acid 3-(4-benzyloxy-phenyl)-isoxazole-5-yl methyl ester (CBT) represented by Formula II below:

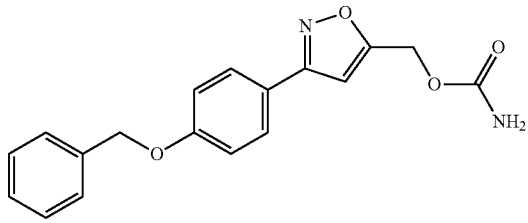

Formula II

Meanwhile, the pharmaceutical composition according to an embodiment of the present invention may include a pharmaceutically acceptable carrier.

The pharmaceutically acceptable carrier in the pharmaceutical composition, which is commonly used in formulation, may include lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but is not limited thereto. The pharmaceutical composition may further include a lubricant, a wetting agent, a sweetener, a flavor enhancer, an emulsifying agent, a suspension agent, and a preservative. Suitable pharmaceutically acceptable carriers and formulations are disclosed in *Remington's Pharmaceutical Sciences* (19th ed., 1995).

The pharmaceutical composition according to an embodiment of the present invention may be administered orally or parenterally. The parenteral administration may include intravenous injection, subcutaneous injection, muscular injection, intraperitoneal injection, endothelial administration, local administration, intranasal administration, intrapulmonary administration, and rectal administration. For the oral administration, an active medicine formed of the pharmaceutical composition may be coated or the pharmaceutical composition may be formulated to prevent the digestion. In addition, the pharmaceutical composition may be administered by a device capable of transferring an active material to a target cell.

A suitable dose of the pharmaceutical composition according to an embodiment of the present invention may depend on many factors, such as formulation methods, administration methods, ages of patients, body weight, gender, pathologic conditions, diets, administration time, administration route, excretion speed, and reaction sensitivity, and a dose of the pharmaceutical composition that is effective to desired treatment or prevention may be easily determined and prescribed by doctors having ordinary skills.

The pharmaceutical composition may be formulated using a pharmaceutically acceptable carrier and/or an additive by a well-known method in the art to be prepared in a unit dose form or to be contained in a multi-dose container. In this regard, the formulation may be a solution in oil or an aqueous medium, a suspension, an emulsifying solution, an extract, powder, granules, a tablet, or a capsule, and may further include a dispersing or stabilizing agent. In addition, the pharmaceutical composition may be administered as an individual drug, or together with other drugs, and may be administered sequentially or simultaneously with pre-existing drugns.

The pharmaceutical composition is used for inhibiting death of neuron or neurodegeneration.

The term "neuron" used herein refers to an animal cell consisting of a cell body, one of protrusions that extrude from the cell body, i.e., an axon or neurite, and several dendrites, and examples of the neuron may include sensory neurons, motoneurons, and interneurons. In addition, the neuron may include neurons constituting a central nervous system, a brain, brain stem, spinal cord and synaptic regions of the central nervous system and peripheral nervous systems, neurosustentacular cells, glia, and Schwann cells.

The term "death of neuron" used herein is interpreted to include death of neurons by apoptosis. In addition, the term "neurodegeneration" used herein means gradual degeneration of the structure or function of neurons, including the death of neurons.

The fact that the apoptosis of a neuron or neurodegeneration cause various brain diseases such as amyotrophic lateral sclerosis, Alzheimer's disease, and Parkinson's disease is well-known in the art, and research regarding mechanism of apoptosis of neurons for prevention or treatment of these diseases has been conducted. *Nature Reviews Molecular Cell Biology* 1:120-130 (2000) and *Journal of Cellular and Molecular Medicine,* 12:2263-2280 (2008) disclose that apoptosis of neurons is the cause of various diseases such as Alzheimer's disease, Parkinson's disease, Huntington's disease, ischemia, a stroke, and sclerosis, and through research regarding mechanism of the apoptosis of neurons causing oxidative stress and dysfunction of mitochondria, a method of preventing or treating neurodegenerative diseases was found. Thus, it is clearly understood by those of ordinary skill in the medical field that a pharmaceutical composition including a compound having an effect of inhibiting apoptosis of neurons or neurodegeneration may be used for prevention or treatment of the diseases described above.

The pharmaceutical composition according to an embodiment of the present invention may be used for neuroprotection.

The term "neuroprotection" used herein means mechanisms within the nervous system which protect neurons from apoptosis or degeneration, and in particular, means effects of reducing, inhibiting or alleviating nerve injuries, and also means effects of protecting, recovering or regenerating neurons in the nervous tissue damaged by nerve injuries. In addition, the term "neuroprotection" is a standard terminology that is generally used by those of ordinary skill in the art to which the present invention pertains (*Neuro Report,* 9:3955-3959 (1998); Chen, J-F., *J. Neurosci.,* 21:RC143 (2001)). The term "protection of a neuron cell" used herein means mechanisms of reducing or ameliorating nervous insult, or mechanisms of protecting or recovering neurons damaged by nervous insult. In addition, the term "nervous insult" used herein means injuries of neurons or nervous tissue caused by various factors (for example, metabolic factor, toxic factor, neurotoxic factor, and chemical factor). Examples of the nervous insult may include oxidative stress, dysregulation of calcium homeostasis, dysfunction of mitochondria, excitotoxicity, caspase activation, and trophic deprivation (*Nature Reviews Molecular Cell Biology* 1:120-130 (2000), *Neurotoxicology and Teratology* 24:675-682 (2002)). The pharmaceutical composition has an effect of inhibiting apoptosis of neurons or neurodegeneration by these various nervous insults or an effect of protecting neurons from the nervous insults. For example, among the nervous insults described above, the oxidative stress is a disease related to apoptosis or degeneration of neurons, and may cause various diseases such as Alzheimer's disease, amyotrophic lateral sclerosis, demyelinating diseases, diabetic polyneuropathy, Down's syndrome, HIV neuropathy, Huntington's disease, multiple system atrophy, Parkinson's disease, stroke and ischemia-reperfusion injury, tauopathy, and traumatic brain damage. Meanwhile, an increase in the activity of an antioxidant enzyme against reactive oxygen species is also known to be one of the mechanisms of neuroprotection (*Free radical Biology & Medicine,* 33(2):182-191 (2002)). Therefore, the pharmaceutical composition inhibits the oxidative stress by inducing a reduction in the reactive oxygen species, thereby preventing apoptosis of a neuron, and thus may be used for prevention or treatment of the various diseases described above.

Accordingly, the pharmaceutical composition may be used as neuroprotective therapeutic agents, which are medicines or chemicals intended to prevent brain or spinal cord from being damaged by ischemia, seizure, convulsion or traumatic injuries.

The pharmaceutical composition according to an embodiment of the present invention may be used for neurorestoration.

The term "neurorestoration" used herein refers to restoration of damaged nervous system by accelerating formation of new synapse connection from neurons. The neurorestoration may mean restoration of dysfunction caused by damaged neurons. For example, the neurorestoration may mean the formation and growth of neurites from a nerve cell, which are for communication with ambient cells, or increasing the number of spines.

The fact that various diseases of the nervous system may be prevented or treated by the neurorestoration is well-known in the art. *Neurotoxicity Research,* 2:71-84 (2000) discloses a possibility of prevention or treatment of particular diseases such as Huntington's disease, Parkinson's disease, amyotrophic lateral sclerosis, and Alzheimer's disease, by medicines used in the neurorestoration, and WO 07/022,182 discloses that diseases such as Huntington's disease, and the like may be treated by neurorestoration of the central nervous system.

As described above, the apoptosis of neurons or neurodegeneration is caused by the various nervous insults, and is related to the various neurodegenerative diseases, and thus the pharmaceutical composition according to an embodiment of the present invention may have an effect of preventing or treating the neurodegenerative diseases by inhibiting the various nervous insults.

The pharmaceutical composition according to an embodiment of the present invention may be used for prevention or treatment of neurodegenerative diseases or ischemia- or repurfusion-related diseases.

Examples of the neurodegenerative diseases, which may be treated by the pharmaceutical composition, may include dementia, Huntington's disease, Parkinson's disease, and amyotrophic lateral sclerosis, but are not limited thereto. In addition, examples of the ischemia- or repurfusion-related diseases, which may be treated by the pharmaceutical composition, may include ischemic stroke, transient ischemic attacks, myocardial ischemia, muscle ischemia, and ischemia caused by surgical techniques regarding extended suspension of blood flow to brain, but are not limited thereto.

The pharmaceutical composition according to an embodiment of the present invention may be used for prevention or treatment of diseases selected from the group consisting of a stroke, Alzheimer's disease, Huntington's disease, Parkinson's disease, Pick's disease, Creutzfeld-Jakob's disease, Parkinson-ALS-dementia complex, Wilson's disease, multiple sclerosis, progressive supranuclear palsy, neuropathic pain-related bipolar disorders, corticobasal degeneration, schizophrenia, attention deficit hyperactivity disorder (ADHD), dementia, amyotrophic lateral sclerosis, retinal disease, epilepsy, apoplexy, transient ischemic attacks, myocardial ischemia, muscle ischemia, ischemia caused by surgical techniques regarding extended suspension of blood flow to brain, a head injury, a spinal cord injury, hypoxia, and depression.

According to an embodiment of the present invention, there is provided a method of treating diseases related to apoptosis of neurons or neurodegeneration, the method including contacting a subject with the pharmaceutical composition. The method may include a method of inhibiting apoptosis of neurons or neurodegeneration, including contacting a subject with the pharmaceutical composition. The diseases may be selected from the group consisting of a stroke, Alzheimer's disease, Huntington's disease, Parkinson's disease, Pick's disease, Creutzfeld-Jakob's disease, Parkinson-ALS-dementi a complex, Wilson's disease, multiple sclerosis, progressive supranuclear palsy, neuropathic pain-related bipolar disorders, corticbasal degeneration, schizophrenia, attention deficit hyperactivity disorder (ADHD), dementia, amyotrophic lateral sclerosis, retinal disease, epilepsy, apoplexy, transient ischemic attacks, myocardial ischemia, muscle ischemia, ischemia caused by surgical techniques regarding extended suspension of blood flow to brain, a head injury, a spinal cord injury, hypoxia, and depression.

The contacting process may be performed in vitro or in vivo, and when the contacting process is performed in vivo, the method may include administering the pharmaceutical composition to a subject.

The subject may be a cell, a tissue, an organ or an individual. In addition, the administering process may be performed by dissolving the pharmaceutical composition in a suitable buffer and then directly contacting a cell, tissue or organ with the resulting solution, or by parenteral administration to an individual. A detailed description of the pharmaceutical composition and administration method thereof used in the method of treating described above is already provided above, and thus is not provided herein to avoid excessive complexity.

The subjects to which the pharmaceutical composition is administered may include all the animals. For example, the animals may be humans, dogs, cats, or mice.

One or more embodiments of the present invention will be described in further detail with reference to the following examples. These examples are for illustrative purposes only and are not intended to limit the scope of the one or more embodiments of the present invention.

BRIEF DESCRIPTION OF DRAWINGS

The above and other features and advantages of the present invention will become more apparent by describing in detail exemplary embodiments thereof with reference to the attached drawings in which.

MODE FOR THE INVENTION

Figure 1:
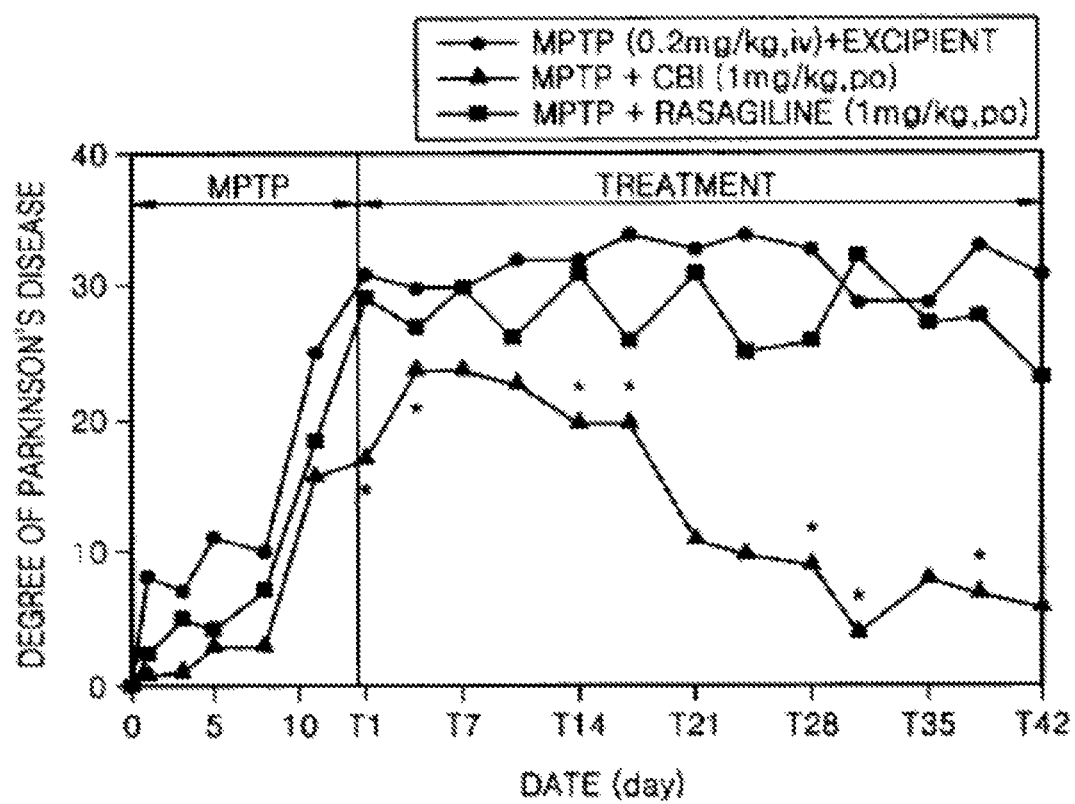
FIG. 1 is a graph showing the degree of Parkinson's disease in a MPTP-induced monkey administered with CBI, according to an embodiment of the present invention.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

EXAMPLE 1

Preparation of carbamic acid 3-(4-benzyloxy-phenyl)-isoxazole-5-yl methyl ester (Formula II)

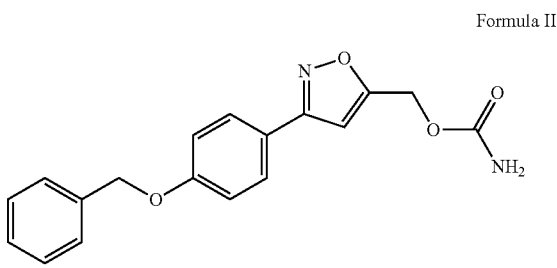 [SMILES: NC(=O)OCc1cc(-c2ccc(OCc3ccccc3)cc2)no1]

Formula II

1.1. Synthesis of 4-benzyloxy-benzaldehyde oxime 4.24 g of 4-benzyloxy benzaldehyde (20 mmol) was dissolved in a 0.2M mixed solution of ethanol and water (3:1, 100 ml), followed by stirring. 2.78 g of $NH_2OH-HCl$ (40 mmol) and 2.46 g of sodium acetate (30 mmol) were added thereto, and stirred at room temperature for about 30 minutes. Subsequently, the completion of the reaction was confirmed by liquid chromatography, and water and ethanol were removed by distillation under reduced pressure to obtain a pale yellow solid compound. The pale yellow solid compound was extracted three times with water and ethyl acetate, an organic solvent layer was dried under reduced pressure to obtain a crude product, and the crude product was then purified with a hexane/ethylacetate solution (10:1) to obtain a white solid compound. The obtained solid compound was subjected to subsequent reactions without additional purification.

1.2. Synthesis of [3-(4-benzyloxy-phenyl)-isoxazole-5-yl]-methanol 2.27 g of 4-benzyloxy-benzaldehydeoxime (10 mmol; 92% purity) was dissolved in 40 ml of methylenechloride (0.25 M), and 1.77 ml of propargyl alcohol (30 mmol) was then added to the resulting solution. 13.7 ml of 10% NaOCl (20 mmol) was then dropwise added very slowly to the resulting solution by using a dropping funnel at 0° C. After the addition of NaOCl was completed, the resulting mixture was stirred for about 5 hours while the temperature was slowly raised to room temperature. Subsequently, the completion of the reaction was confirmed by liquid chromatography, the resultant was subjected to distillation under reduced pressure to evaporate methylenechloride therefrom, 200 ml of water was added to the residue, and the obtained solid was then filtered. The filtered compound was washed with a large amount of water, and then washed with diethylether to obtain a solid compound. The obtained solid compound was purified with an ethylacetate/hexane solution (1:2) to obtain a white, solid [3-(4-benzyloxy-phenyl)-isoxazole-5-yl]-methanol (yield: 2.5 g).

$^1$H-NMR ($CDCl_3$,200 MHz) δ7.7(d,2H), 7.4(m,4H), 7.1 (d,2H), 6.5(s,1H), 5.1(s,2H), 4.8(s,2H)

1.3. Synthesis of carbamic acid 3-(4-benzyloxy-phenyl)-isoxazole-5-yl methyl ester 1.04 ml (12 mmol) of chlorosulfonyl isocyanate was slowly added at −78° C. to a solution of THF (50 ml, 0.2M) and [3-(4-benzyloxy-phenyl)-isoxazole-5-yl]-methanol (2.813 g, 10 mmol), put in a 250 ml flask. Subsequently, the complete removal of a starting material was confirmed by liquid chromatography, and water was then added to the resulting reaction solution. After one hour, the resulting solution was subjected to distillation under reduced pressure to evaporate THF therefrom, 100 ml of water was added to the resultant, and the obtained solid was filtered. The filtered solid was washed with 100 ml of water and an ethylacetate/hexane solution (1:2), respectively, and dried to obtain 3.4 g of a crude product (purity:95.9%). The crude product was purified in an ethylacetate/hexane/methylenechloride (1:4:1) solution containing 1% methanol to 2.743 g of carbamic acid 3-(4-benzyloxy-phenyl)-isoxazole-5-yl methylester (CBI) with a purity of 99%.

$^1$H-NMR ($CDCl_3$,200 MHz) δ7.7(d, 2H), 7.4 (m, 4H), 7.1 (d, 2H), 6.6 (s, 1H), 5.2 (s, 2H), 5.1 (s, 2H), 4.8 (brs, 2H)

EXAMPLE 2

Confirmation of Neuroprotective Effect of CBI by Using MPTP-induced Monkey 1-methyl-4-phenyl-1,2,3,6-tetrahydropyridine (MPTP) is reported to induce clinical, biochemical and pathologic characteristics similar to those observed in patients with Parkinson's disease, and is known as a neurotoxin that is widely used in preparing an animal model for Parkinson's disease in rodents and primates (J. Neural Transm., 103:987-1041 (1996); Neurotoxicol. Teratol. 24:607-620 (2002)). MPTP is converted to 1-methyl-4-phenyl-pyridinium ($MPP^+$) by monoamineoxidase (MAO)-B, and $MPP^+$ has a high affinity for the dopamine transporter (DAT) and induces dysfunction of mitochondria and oxidativestress, resulting in apoptosis of dopaminergic neurons that induce the formation of dopamine (J. Neurochem., 61:1191-1206 (1993); J. Neural Transm., 103:987-1041 (1996); Mov. Disord., 13:35-38 (1998); Restor. Neurol. Neurosci., 16:135-142 (2000)).

Macaque monkeys (n=35, 3 to 4-year-old) were used as an experimental model. The macaque monkeys were divided into three groups, and 0.2 mg/kg of MPTP was administered to each group (once a day, every day, until Parkinson's disease score reaches 8 or for 14 days) via intravenous injection. Next day after the 14 day administration, an excipient (control), 1 mg/kg of CBI, and 1 mg/kg of rasagiline (prepared using a method of preparing R(+)-N-propargyl-1-aminoindan rasagiline, disclosed in U.S. Pat. No. 5,457,133) were respectively administered orally to the three groups for 4 weeks, and changes of the Parkinson's disease score were measured. In addition, to confirm the effect of CBT as a dopamine agonist, dopamine transporters existing in medial striatum and caudal striatum taken from the MPTP-induced monkey model were subjected to a dopamine transporter binding assay.

EXAMPLE 2-1

Measurement of the Extent of Parkinson's Disease

The extent of Parkinson's disease was measured by analyzing videotaped behaviors of each group of monkeys, based on four standards: a) range of movement, b) hypokinesia, c) extent of abnormal posture, and d) tremor. A Parkinson's disease score was evaluated by the sum of (4-range of movement)+hypokinesia+extent of abnormal posture+tremor. Hence, the maximum value of the total Parkinson's disease score is 10. The Parkinson's disease score was measured for 10 minutes every 30 minutes through 2 hours. That is, the maximum value of the highest Parkinson's disease score is 40. Meanwhile, the measurement method performed based on the four standards was as follows, and evaluated scores below represent representative behaviors observed through observation periods:

a) Score of the range of movement: 0=no movement; 1=only movement of head; 2=movement of head, limbs and/or body without exercise no shorter than 30% of the observation time; 3=walking/walking or climbing the wall of a cage no longer than 30% of the observation time; 4=walking/walking or climbing the wall of a cage no shorter than 30% of the observation time.

b) Score of hypokinesia: 0=normal speed of movement and beginning of normal movement; 1=slight slowness of movement; 2=medium-speed of slow movement, difficult to begin and maintain movement, obvious stiffness of the body; 3=inability of exercise, continuous stiffness of the body, resulting in inability of movement.

c) Score of the extent of abnormal posture: 0=normal, good posture, possible to raise its head, normal balance; 1=bent body, possible to raise its head; 2=bent body, impossible to raise its neck and head, loss of balance.

d) Score of tremor: 0=none; 1=existing.

As a result of the measurement of the extent of Parkinson's disease, it was confirmed that the group of monkeys administered with CBI exhibited a significantly decreased extent of Parkinson's disease, compared with the group of monkeys administered with rasagiline known as a medicine used in the treatment of Parkinson's disease (refer to FIG. 1).

EXAMPLE 2-2

Analysis of Dopamine Transporter Binding

A brain was taken out of each group of monkeys, the brain stem was separated therefrom, and a cerebral hemisphere was then divided into two along a median line. A tissue was immersed in isopentane at −45° C., immediately frozen, and then stored at −80° C. The coronal section of the cerebral hemisphere was prepared to a thickness of 20 in a cryostat at −17° C., and then defrosted. The defrosted resultant was mounted on a slide coated with gelatin, dried thereon, and then stored at −80° C.

For dopamine transporter binding, labeling with a radioactive element of [$^{125}$I]-(E)-N-(3-iodopro-2-phenyl)-2βcarboxymethyl-3β(4'-methylphenyl)-nortropane (PE2I) was performed using a stannyl precursor according to a conventional method used for confirming a dopamine nerve terminal (D. Guilloteau et al., 1998). The resultant was purified to obtain a no-carrier-added form of [$^{125}$I]PE2I having an activity of 2000 Ci/mmol. The coronal section of the cerebral hemisphere was incubated with 100 pM [$^{125}$I]PE2I in a pH7.4 phosphate buffer (NaH$_2$PO$_4$ 10.14 mM, NaCl 137 mM, KCl 2.7 mM, KH$_2$PO$_4$ 1.76 mM) at 25° C. for 90 minutes, by using a method disclosed in the related art (S. Chalon et al., 1999; E. Bezard et al., 2001). The adjacent section was incubated in the presence of 100 of cocaine (Sigma, St Louis, Mo.), and thus non-specific binding was confirmed. After the incubation, the section was washed twice with a phosphate buffer at 4° C. for 20 minutes, and rinsed with distilled water at 4° C. for one second. The resulting section was dried at room temperature, and then exposed to β radiation-sensitive film (Hyperfilm B max, Amersham, Buckinghamshire, UK), together with calibrated [$^{125}$I]-microscales (Amersham) in x-ray cassettes for 3 days, and thus radioactivity bound to desired regions was measured.

Figure 2:
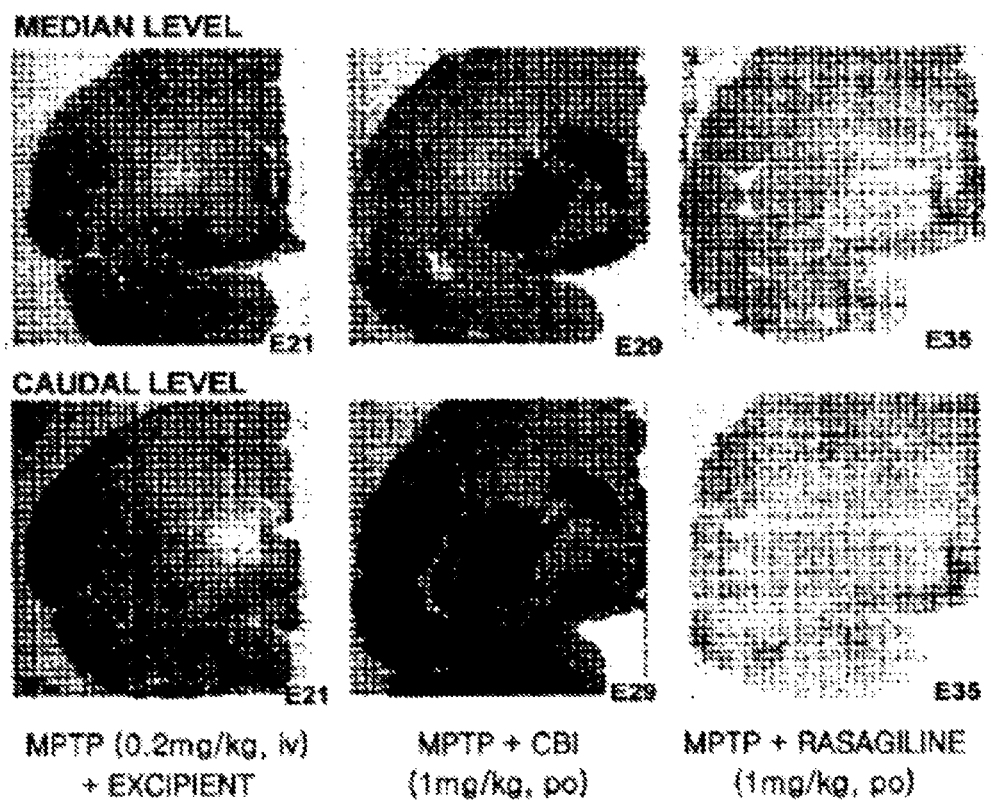
FIG. 2 illustrates microscopic images showing whether or not a dopamine transporter exists in central striatum and tail striatum of a MPTP-induced monkey administered with CBI, according to an embodiment of the present invention.

As shown in FIG. 2, the group of monkeys administered with CBI exhibited a large number of dopamine transporters in their medial striatum and caudal striatum, and exhibited a significantly larger amount of dopamine transporters than that exhibited by the group of monkeys administered with the same amount of rasagiline as that of CBI. This result indicates that CBT effectively inhibits apoptosis of dopaminergic neurons, and thus the loss of dopamine transporters by MPTP is relatively lower than that in the control or the group of monkeys administered with rasagiline. From the results, it was confirmed that CBI is capable of implementing neuroprotection, including inhibiting progression of Parkinson's disease.

EXAMPLE 3

Neuroprotective Effect of CBI by Using MPTP-induced Mouse Model

C57BL/6 mice (n=94, 8-week-old; male) were used as an experimental model (substrain: C57BL/6NCrljBgi, ORIENT BIO INC.). 30 mg/kg of MPTP was administered to the mice via intraperitoneal injection once a day for 4 days. 4 days after the last day of administration, the mice were divided into three group, and an excipient (control), 1 mg/kg of CBI, and 1 mg/kg of rasagiline were respectively administered orally to the three groups once a day for 10 days. Next day after the last day of administration, a tail suspension test (TST) was performed on each group, and striatum and substantia nigra brain tissue were taken out from each group of mice, and thus the concentrations of dopamine and metabolic product thereof in striatum and the extent of a decrease in neurons in substantia nigra were measured.

EXAMPLE 3-1

Analysis of Behaviors of Mice by Tail Suspension Test

The tail suspension test was performed to measure the extent of causation of behavioral loss according to the administration of MPTP and medicines. The TST was performed in such a manner that 7 days after the compounds described above are respectively administered to the three groups, a circular stainless steel stick with a width of 1 cm was fixed to a cage with a width of 16 cm and a height of 40 cm located at a height of 35 cm and whose left and right sides were covered by black wood. The movement time of the mice was measured for 6 minutes in a second unit, and thus the efficacies of the compounds were evaluated.

Figure 3:
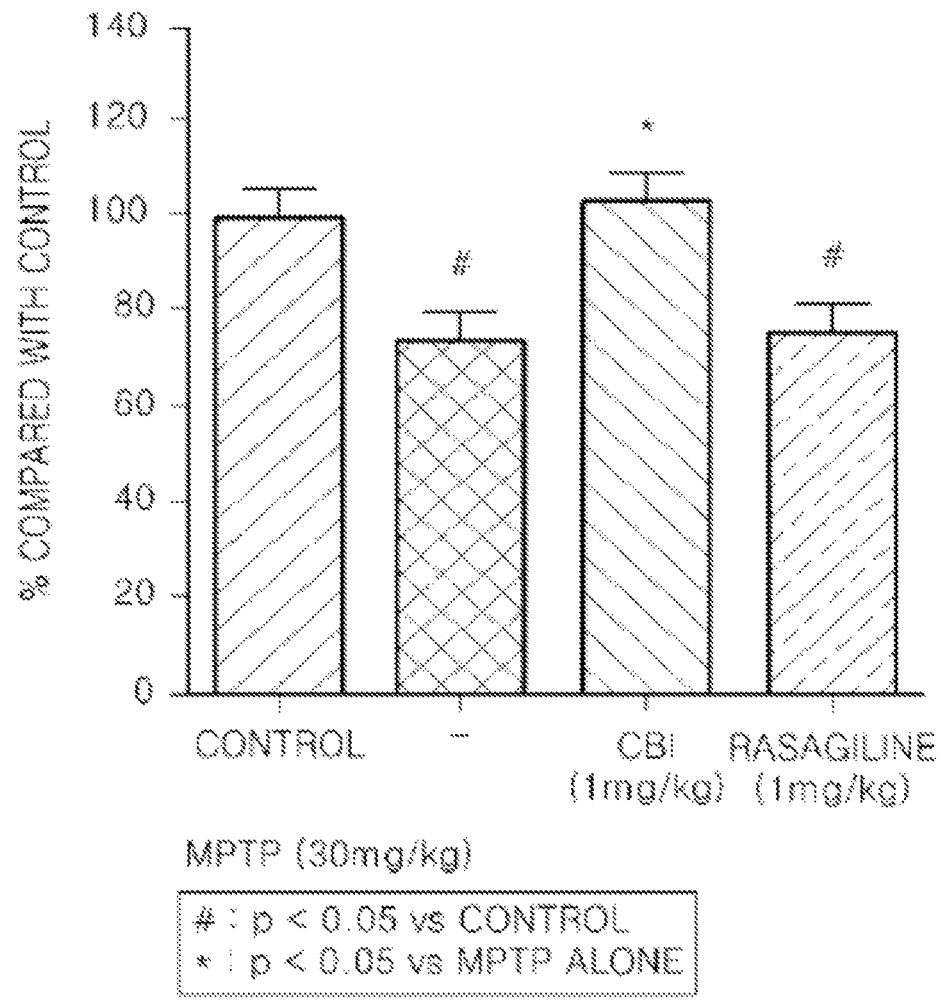
FIG. 3 is a graph showing tail suspension test results of a MPTP-induced mouse administered with CBI, according to an embodiment of the present invention.

As a result of the TST analysis, it was confirmed that while the group of mice administered with MPTP exhibited meaningful behavioral loss, the group of MPTP-induced mice administered with CBI exhibited the same extent of behaviors as those of normal mice, and exhibited an excellent capability of behavioral restoration, compared with the group of MPTP-induced mice administered with rasagiline (refer to FIG. 3).

EXAMPLE 3-2

Measurement of Amounts of Dopamine and Metabolic Product thereof in Striatum

A change in the amounts of dopamine and metabolic product thereof in striatum according to the administration of MPTP and the compounds described above was measured by high performance liquid chromatography (HPLC). 7 days after the compounds described above are respectively administered to the three groups, the mice in each group were sacrificed by cervical dislocation and brain tissues were immediately taken out of the mice. Striatum was collected from the brain tissue, 0.5 ml of a HPLC assay diluent (0.1 M $HClO_4$, 0.1 mM EDTA) was added to the striatum, and a tissue homogenate was then prepared using an ultrasonic processor. The homogenate was centrifuged at 12,000 rpm for 15 minutes, and the supernatant was filtered with a nitrocellulose filter (0.2 um, Millipore). For HPLC analysis, HR-80 column (80 mm×4.6 mm, particle size: 3 μm ESA, USA) was used, the flow rate of a mobile phase (0.07 M monobasic sodium phosphate, 1 mM sodium octasulfonic acid, 0.1 uM EDTA, 5% acetonitrile, pH 3.2) was maintained at 0.7 ml/min, and the electrode potential of an electrochemical detector (Coulochem III, ESA, USA) was at $E1=-100$ mV, $E2=350$ mV.

Figure 4:
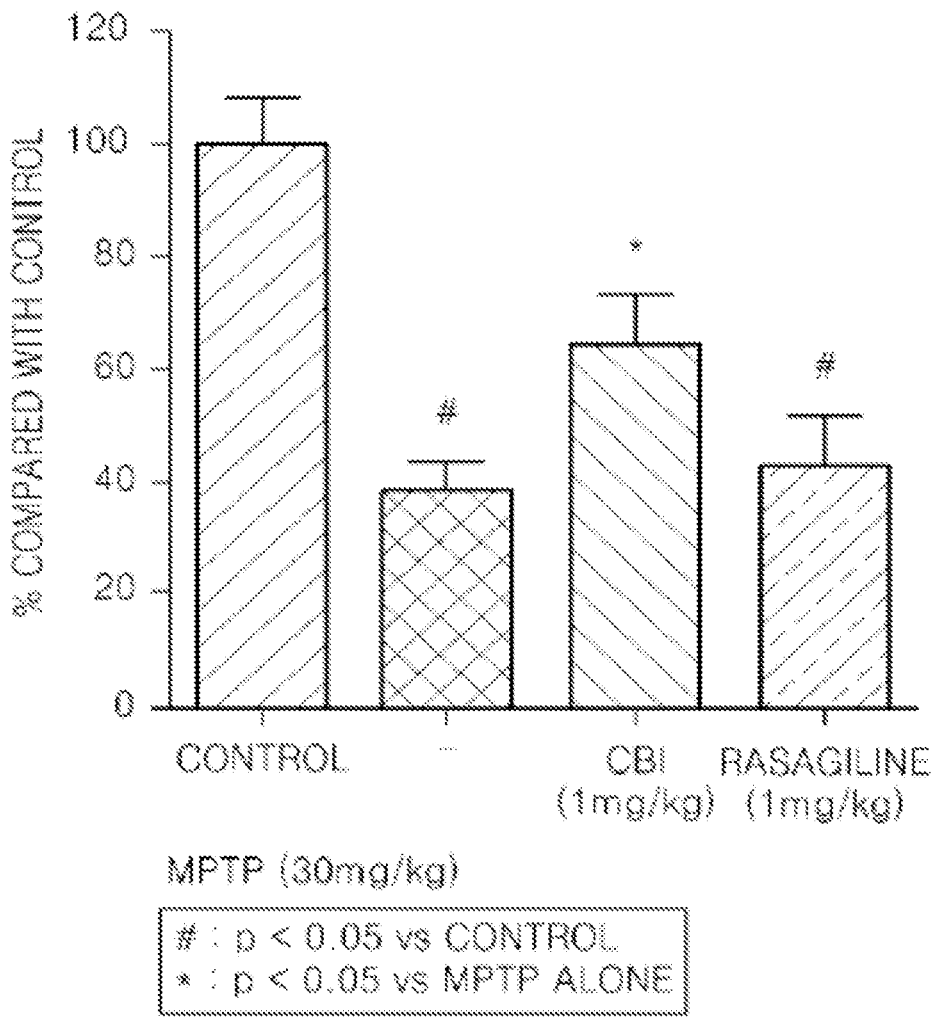
FIG. 4 is a graph showing the concentration of dopamine in striatum of a MPTP-induced mouse administered with CBI, according to an embodiment of the present invention.

As a result of analyzing the concentration of dopamine in striatum through the experiment, it was confirmed that the group of mice administered with rasagiline exhibited restoration of the concentration of dopamine to about 40% compared with normal mice, while the group of MPTP-induced mice administered with CBT exhibited restoration of the concentration of dopamine to about 70% compared with normal mice (refer to FIG. 4).

EXAMPLE 3-3

Immunohistochemistry Staining by Using Antibody for Tyrosine Hydroxylase

A change in the expression of an antibody against tyrosine hydroxylase in striatum and substantia nigra according to the administration of the compounds described above was measured by immunohistochemistry staining. Each group of mice was anesthetized with sodium pentobarbital (50 mg/kg), the thorax of the mouse was opened, and 200 ml of 0.1 M PBS (pH 7.4) was perfused into the heart, thereby removing blood in blood vessels. After blood was fully removed, 250-300 ml of a 4% paraformaldehyde/PBS fixation solution was perfused into the heart, the brain was taken out, and the brain was subjected to postfixation with the paraformaldehyde/PBS fixation solution in a refrigerated condition for 24 hours. Subsequently, the brain tissue was thoroughly washed with PBS to remove the fixation solution, and to prevent ice crystals produced during freeze, the resulting brain tissue was placed into a 30% sucrose solution and stored therein until it sank. The resulting tissue was embedded with an embedding agent for freeze (OCT compound) and frozen at $-40°$ C., and the successive coronal section of a midbrain region containing striatum and substantia nigra was prepared to a thickness of 40 μm using Cryostat (Reichert Frigocut model 2000). The coronal section was maintained in 3% $H_2O_2$/PBS for 30 minutes, and then maintained in 0.1 M PBS containing 0.3% Triton X-100 and 3% bovine serum albumin for 30 minutes. To selectively stain cells containing dopamine, the section was reacted with anti-mouse monoclonal TH (Chemicon International, Temecula, Calif.; 1:500) as a primary antibody at room temperature over night, and biotinylated goat anti-mouse IgG (Vector Lab, Burlingame, Calif., 1:200) was used as a secondary antibody. Subsequently, avidin-biotin binding was induced using Vectastain elite ABC kit (Vector Lab, Burlingame, Calif.), and color development was performed on the tissue by using 3,4-diaminobenzidine (DAB). The resulting tissue was placed in PBS, it was mounted on a slide glass, and the resultant was dried and then covered by a cover glass. The substantia nigra of the midbrain region in the resultant was observed using a microscope equipped with a digital camera (Olympus BX-60, Olympus Optical, Tokyo, Japan) at a magnification of 200×, cells that exhibited a positive reaction to the antibody against tyrosine hydroxylase were observed and recorded, and statistical analysis (One-way ANOVA) was conducted using a Graph pad Prism 4 program.

Figure 5:
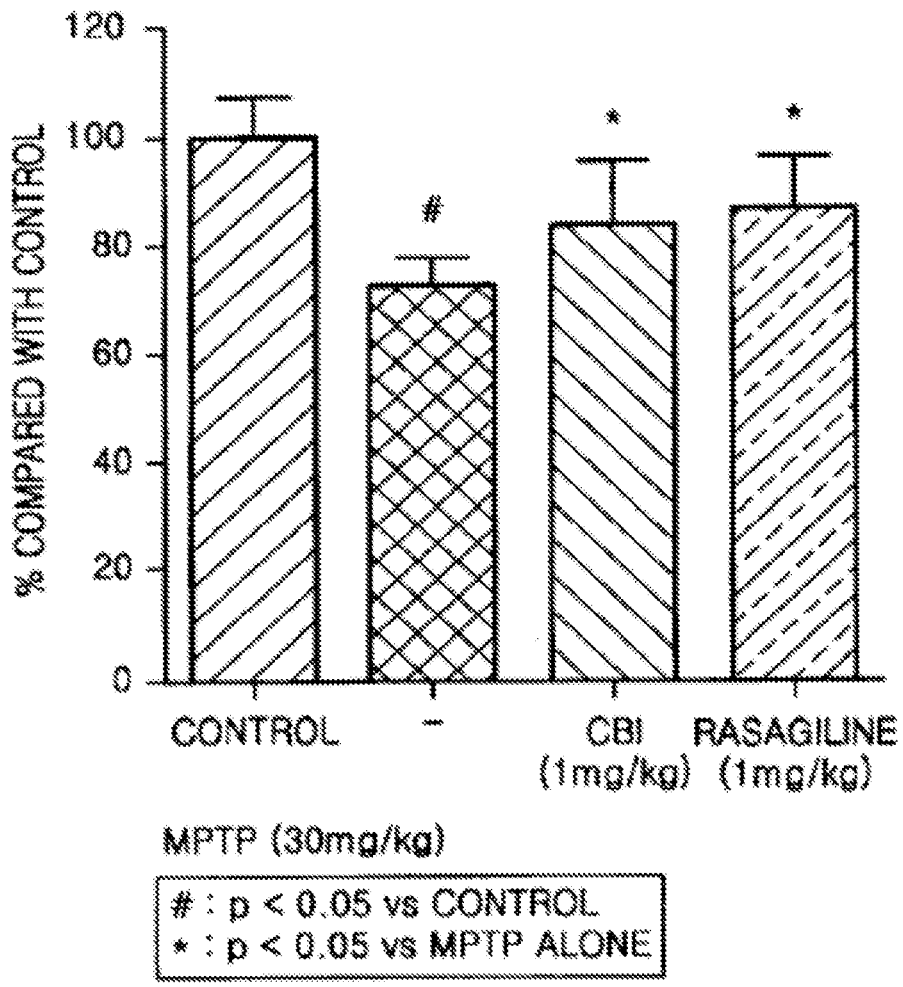
FIG. 5 is a graph showing the degree of a decrease in neurons of substantia nigra of a MPTP-induced mouse administered with CBI, according to an embodiment of the present invention.

As a result of analyzing the extent of a decrease in neurons in substantia nigra by immunohistochemistry staining using the antibody against tyrosine hydroxylase as described above, the group of MPTP-induced mice administered with CBT exhibited the same extent of a decrease in neurons in substantia nigra as that in the group of MPTP-induced mice administered with rasagiline (refer to FIG. 5). From the results, it was confirmed that CBI functions as a dopamine agonist, thereby being capable of implementing neuroprotection, and has a superior effect to rasagiline, which is conventionally known as a dopamine agonist.

EXAMPLE 4

Confirmation of Neuroprotective Effect of CBI by Using 6-OHDA-induced Rat Model 6-hydroxydopamine (6-OHDA) is known as a neurotoxin that increases the formation of hydroxyl radicals, thereby inducing the degeneration of neurons of substantia nigra and striatum. The hydroxyl radicals rapidly destroy the terminal region of a neuron (*J. Neural. Transm.*, 103:987-1041 (1996); *J. Neurosci.*, 19:1284-1293 (1999)), thereby causing gradual loss of cells in substantia nigra pars compacta (SNpc), and such loss is known to be similar to gradual degeneration of substantia nigra and striatum, observed in patients with Parkinson's disease in early stages (*Brain Res.*, 26:301-307 (1991); *Neurosci.*, 59:401-415 (1994); *Neurosci.*, 67:631-647 (1995); *Neurosci.*, 72:641-653 (1996)).

Wistar rats provided by ORIENT BIO INC. (excipient and CBI n=7, rasagiline n=6; 6-week-old; 20 male rats) were used as an experimental model. One-side injection of 3 μl of a solution containing 20 μg/μl of 6-OHDA was performed on the striatum of each rat (position: front—1.0 mm, rear—3.0 mm, postabdomen side—5.0 mm), thereby inducing the degeneration of neurons in the striatum. The rats were divided into three groups, and an excipient (control), 1 mg/kg of CBI, and 1 mg/kg of rasagiline were respectively administered orally to the three groups 1 hour before administration of 6-OHDA and once every other day for 6 weeks. 4, 5 and 6 weeks after the last day of administration, an apomorphine-induced rotation test was performed on each group. The apomorphine-induced rotation test was performed in such a manner that 0.5 mg/kg of apomorphine was administered to each group of rats via intraperitoneal injection, each group of rats was placed in a rotor chamber, and the rotary movement thereof was recorded for 45 minutes, and thus the number of rotation per minute of each group of rats was measured to determine the average value thereof. In addition, after the apomorphine-induced rotation test performed 6 weeks after the last day of administration, each group of rats was sacrificed, and thus the extent of a decrease in neurons of substantia nigra pars compacta was confirmed using immunohistochemistry staining using an antibody against tyrosine hydroxylase and cresyl violet staining. As described in Example 3-3 above, a successive coronal section of a midbrain region containing substantia nigra was prepared, the section was put in PBS, the resulting section was attached to a silane-coated slide glass and dried, and the slide glass was then placed in xylene, 100% alcohol, 95% alcohol, 70% alcohol and distilled water for 5 minutes, 2 minutes, 1 minute, 1 minute and 2 minutes, respectively. Subsequently, the resulting slide glass was immersed in a 1% cresyl violet solution for 5 minutes and washed with distilled water, 70% alcohol, 95% alcohol, 100% alcohol and xylene for 2 minutes, 1 minute, 1 minute, 2 minutes and 5 minutes, respectively, and the slide glass was covered by a cover glass and observed using a microscope equipped with a digital camera (Olympus BX-60, Olympus Optical, Tokyo, Japan). The substantia nigra of the midbrain region was observed at a magnification of 200×, cells that exhibited a positive reaction to cresyl violet were observed and recorded, and statistical analysis (One-way ANOVA) was then conducted using a Graph pad Prism 4 program.

Figure 6:
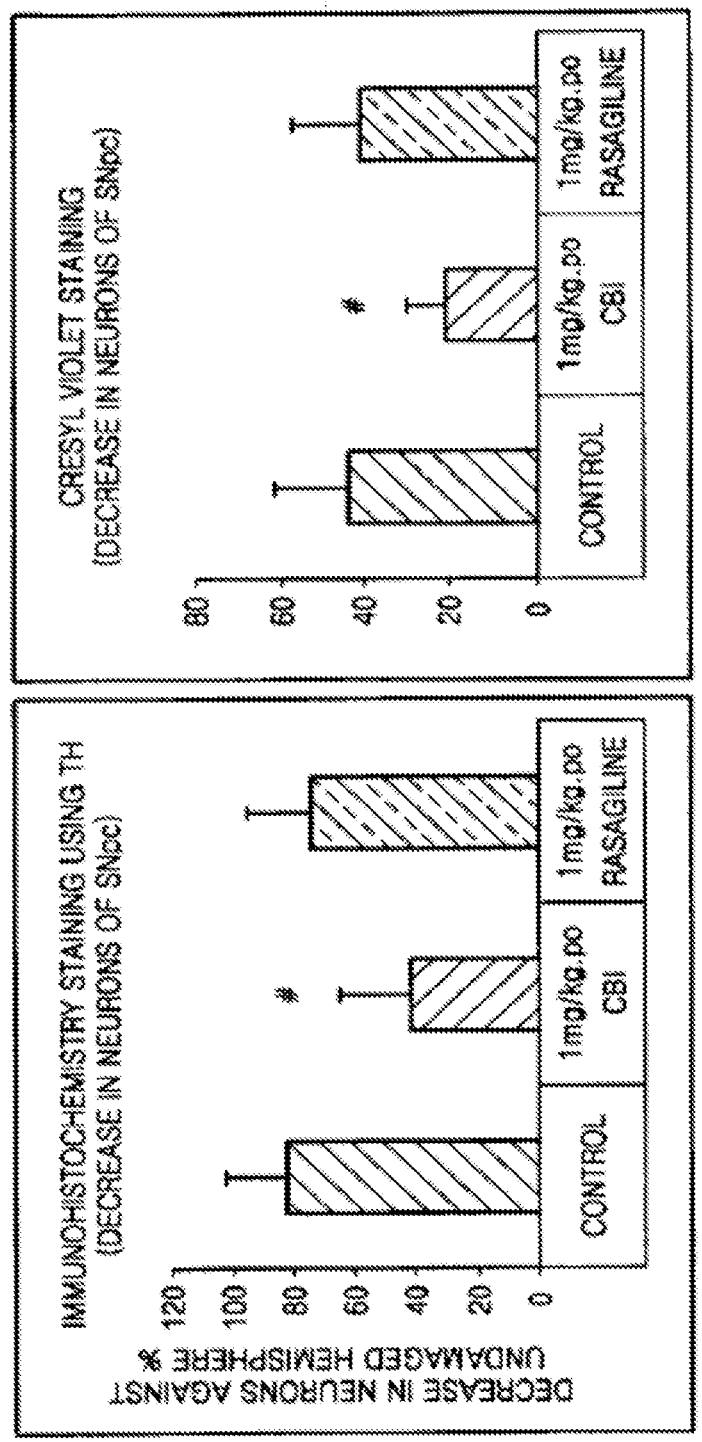
FIG. 6 illustrates graphs showing the degree of a decrease in neurons of substantia nigra compactum of a 6-OHDA-induced rat administered with CBI, observed by immunohistochemistry staining using tyrosine hydroxylase as an antibody and cresyl violet staining, according to an embodiment of the present invention.

As shown in FIG. 6, it was confirmed that the group of 6-OHDA-induced rats administered with CBI exhibited a significantly decreased extent of a decrease in neurons, and had a superior effect to that in the group of 6-OHDA-induced rats administered with rasagiline.

EXAMPLE 5

Confirmation of Neuroprotective Effect of CBI by Using Malonate-induced Mouse Model Malonate is a reversible inhibitor of succinate dehydrogenase, which is an enzyme of mitochondria, and known to inhibit the electron transport system of mitochondria to induce the degeneration of excitotoxic neurons, or to increase the release of dopamine from striatum to cause the loss of the striatum. A deficiency of bioenergy in mitochondria is associated with pathologic phenomenon of various neurodegenerative diseases such as Parkinson's disease, Huntington's disease, Alzheimer's disease and amyotrophic lateral sclerosis (*Ann. Neurol.*, 58:495-505 (2005); *Nat. Rev. Neurosci.*, 7:278-294 (2006)), and the injection of malonate into the striatum of an animal causes loss similar to that observed in focal ischemia or Huntington's disease (*Experimental Neurology*, 178:301-305 (2002)). This causes metabolic stress to several groups of neurons, resulting in a decrease in the amount of dopamine of both the cell body of a substantia nigra dopamine cell and striatum (*J. Neurochem.*, 61:1147-1150 (1993); *Brain Res.*, 773:223-226 (1997); *Neuroscience*, 96:309-316 (2000)).

ICR mice (n=34, 10-week-old; male) were used as an experimental model. 5 ml/kg of equithesin was administered to each mouse via intraperitoneal injection to be anesthetized, two levelers of a stereotactic instrument were set at 0 mm from both external auditory canals, and the skull of the mouse was perforated in the stereotactic instrument. 0.2 mg/ml of ascorbic acid was used as a control, and 2.4 umole/2 of malonate was injected into a lesion group and a compound treatment group 0.5 mm forward (AP) and 1.2 mm sideward from striatum on the right side (bregma) and 3.1 mm downward from dura matter by using a Hamilton syringe (10 μl, 26G needle) at a rate of 1 uL/min. The groups administered with malonate were divided into two groups, and 0.5 ml/kg of excipient (n=12) and 5 mg/kg of CBI (n=14) were respectively administered to the two groups via intraperitoneal injection 2 hours before an operation and administered again 1 hour, 1 day, 2 days and 3 days after the operation, i.e., total five times. Malonate was injected into striatum of the mouse, the mouse was sacrificed after 3 days, and the brain was taken out of the mouse to prepare a section. Thereafter, the section was stained with 2,3,5-triphenyltetrazolium chloride (TTC).

Figure 7:
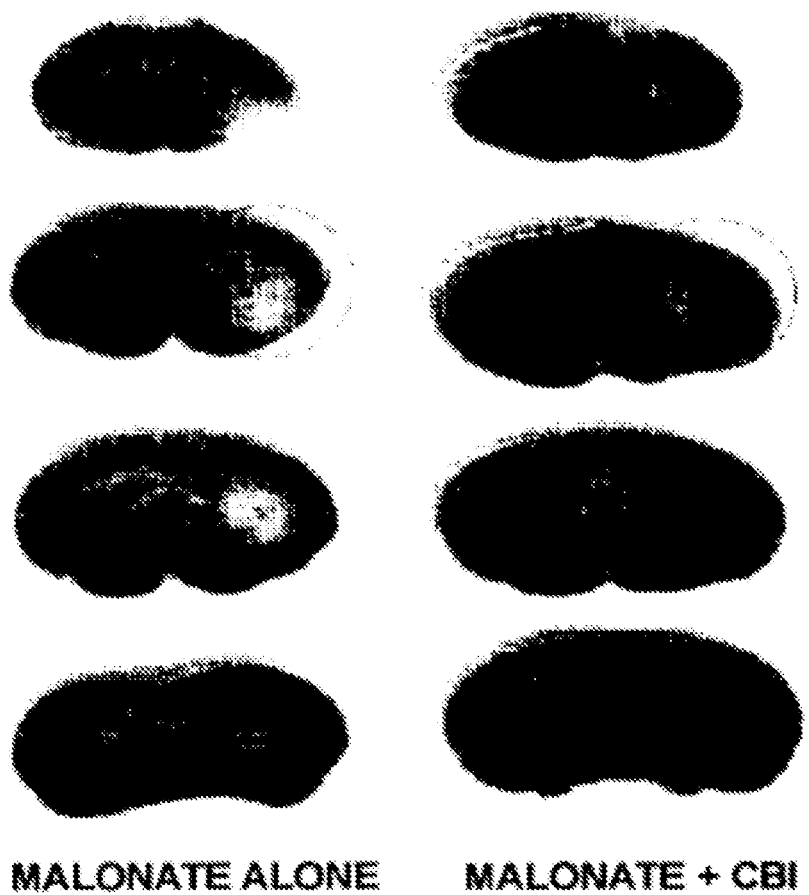
FIG. 7 illustrates images showing whether or not striatum of a malonate-induced mouse administered with CBI recovers from damage, according to an embodiment of the present invention.
Figure 8:
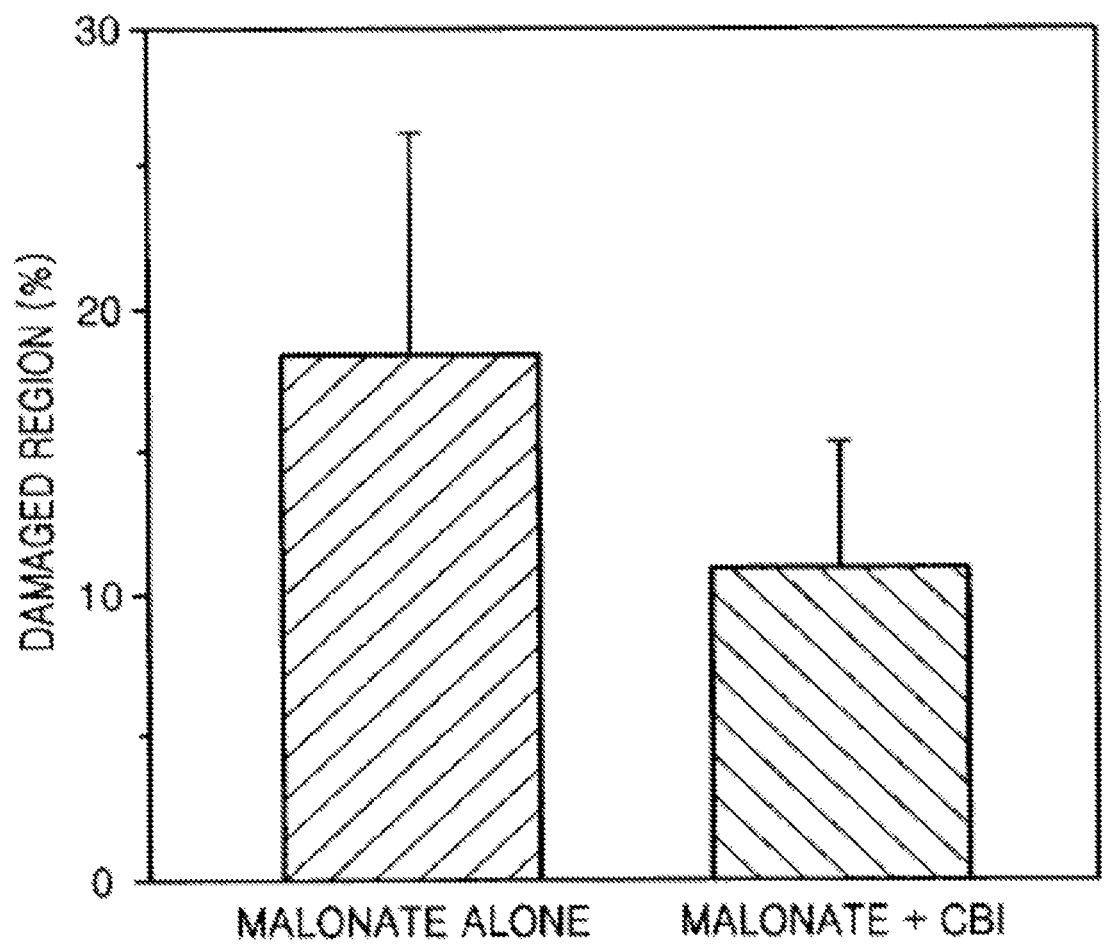
FIG. 8 is a graph showing the degree of recovery of damaged striatum of a malonate-induced mouse administered with CBI recovers from damage, according to an embodiment of the present invention.

As shown in FIGS. 7 and 8, it was confirmed that CBI inhibited apoptosis of neurons in striatum induced by malonate, thereby significantly reducing damaged regions of the striatum. Thus, the result indicates that CBI alleviates apoptosis of neurons caused by damage of mitochondria.

EXAMPLE 6

Confirmation of Neuroprotective Effect of CBI by Anti-apoptosis of Neurons

Many neurodegenerative diseases such as a stroke, brain injuries, spinal cord injuries, amyotrophic lateral sclerosis, Huntington's disease, Alzheimer's disease, and Parkinson's disease are characterized in apoptosis of neurons (*The New England Journal of Medicine*, 348:1365 (2003)), and chronic neurodegenerative diseases are known to be caused by the induction of apoptosis pathways by several internal or external factors. To explain biochemical and molecular biological changes occurring in apoptosis of neurons, approach into searching for materials exhibiting multidirectional mechanisms in several steps of the apoptosis of neurons or treatment of neuroprotective medicines has been underway (*CNS drugs*, 19:723 (2005); *Nat. Rev. Neurosci.*, 7:295 (2006)).

Referring to FIGS. 6 though 10, it is confirmed that CBI inhibits the apoptosis of neurons caused by the several internal or external factors, thereby exhibiting a therapeutic effect on neurodegenerative diseases.

In this embodiment, MAO-B-deficient human neuroblastoma SH-SY5Y cells (Korean Cell Line Bank) were used. Apoptosis of the human neuroblastoma cells was induced by serum starvation. The MAO-B-deficient human neuroblastoma SH-SY5Y cells cultured in a normal medium were distributed into a 6-well plate at a concentration of $1.8 \times 10^5$ cells/well and incubated for 1 day, the medium was exchanged with a serum-free medium containing CBI (0.1, 1 and 10), a serum-free medium containing rasagiline (0.1, 1 and 10), or a serum-free medium containing neither CBI or rasagiline, and the cell was further incubated in 5% $CO_2$ at 37° C. for 48 hours. Subsequently, the number of dead cells was represented as a percentage, compared with a control that did not cause the apoptosis of neurons.

Figure 9:
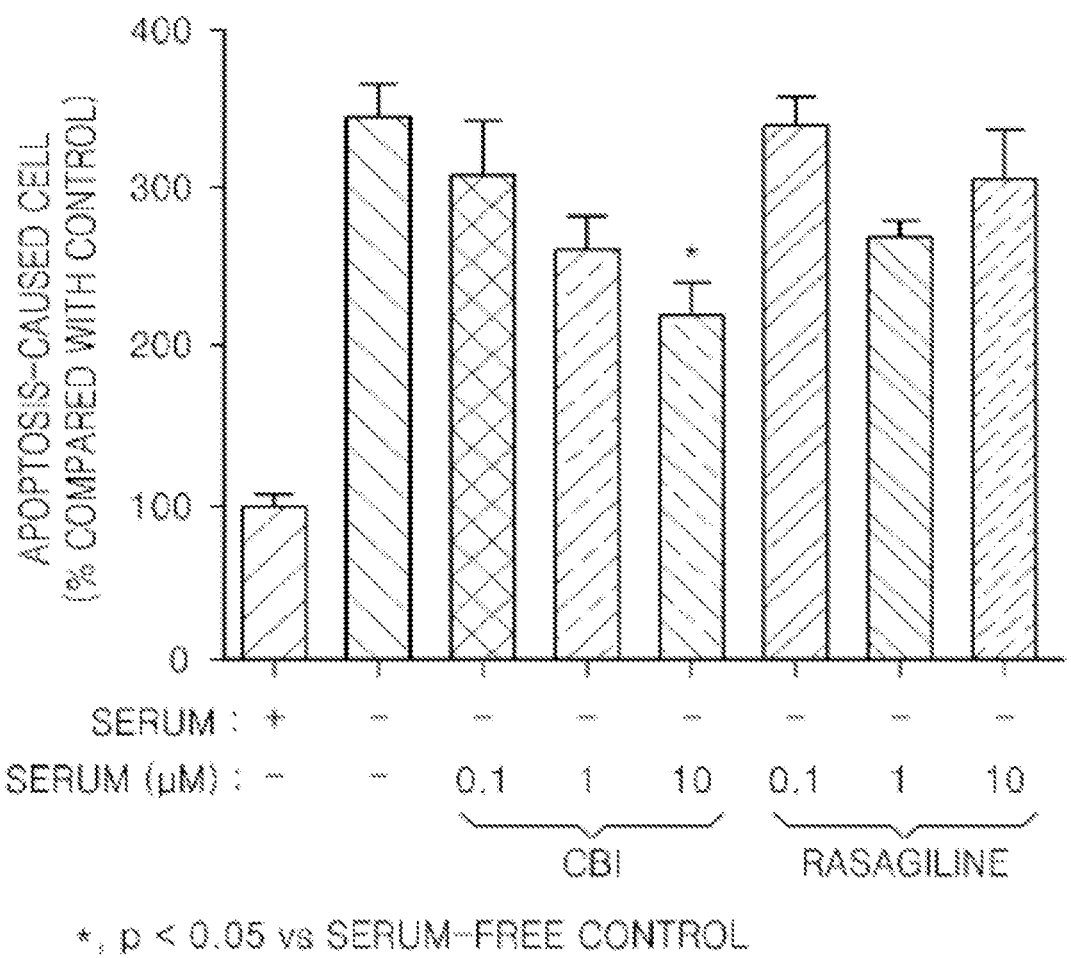
FIG. 9 is a graph showing the degree of apoptosis in MAO-B-deficient SH-SY5Y cells treated with CBI, according to an embodiment of the present invention.

As shown in FIG. 9, it was confirmed that when the apoptosis-induced neuron was administered with CBI, the extent of the apoptosis of neurons was decreased. In particular, it was confirmed that when the apoptosis-induced neuron was administered with 10 of CBT, it exhibited a higher extent of a decrease in the apoptosis of neurons, i.e., about 33% than that in the case of the apoptosis-induced neuron administered with 10 of rasagiline.

Meanwhile, a variety of signal transduction proteins are involved in a process for mediating or inhibiting apoptosis, and representative examples thereof include Bcl-2 gene family proteins (*Journal of Bioenergetics and Biomembranes*, 37:179-190 (2005); *J. Cell Mol. Med.*, 7:249-257 (2003); *Genes and Development*, 13:1899-1911 (1999)). Thus, 0.1, 1 and 10 of CBI or 0.1, 1 and 10 of rasagiline were respectively added to the apoptosis-induced cells as described above, the resulting cells were further incubated in 5% of $CO_2$ at 37° C. for 24 hours, mRNA was extracted from the cultured cells or a cell extract was obtained therefrom, and thus the amount of Bcl-2 mRNA and the amounts of Bcl-2 and Bcl-xL proteins were measured. The amount of Bcl-2 mRNA was measured by real-time RT-PCR, and the amounts of Bcl-2 and Bcl-xL proteins were measured by western blotting.

The total RNA of the SH-SY5Y cell was extracted using RNeasy MiniKit (Qiagen) after the SH-SY5Y cell was treated with CBI or rasagiline in a serum-free medium for 24 hours. 2 ug of the total RNA was reverse transcribed using High Capacity cDNA Reverse Transcription Kit (Applied Biosystems), and real-time PCR (Applied Biosystems, 7500 Real Time PCR SYSTEM) was performed thereon by using a TaqMan probe (Applied Biosystems, USA) for Bcl-2. As an internal control, mRNA for 18SRNA was amplified. The relative quantification of mRNA levels of target genes was determined by ddCt method (Takekawa, 1998).

For western blotting, the SH-SY5Y cells were lysed with RIPA buffer (50 mM Tris-Cl pH 7.4, 1% NP-40, 0.25% sodium deoxycholate, 0.1% SDS, 150 mM NaCl, 1 mM EDTA) and then centrifuged to obtain a cell extract. Subsequently, the cell extract was quantified, the same amount of the cell extract was loaded onto a SDS-PAGE gel followed by electrophoresis, the gel was transferred onto a nitrocellulose membrane, the membrane was blotted using an antibody against Bcl-2 (Cat#: 2872, Cell Signaling, USA) and an antibody against Bcl-xL (Cat#: 2762, Cell Signaling, USA) that were respectively diluted to 1:5000 by using a well-known method in the art, and the expression amounts of Bcl-2 and Bcl-xL proteins were confirmed using ECL kit (Amersham Pharmacia). An antibody against β-actin (Cat#: A2228, Sigma, USA) was used as a control, and the expression amount of β-actin protein was confirmed.

Figure 10:
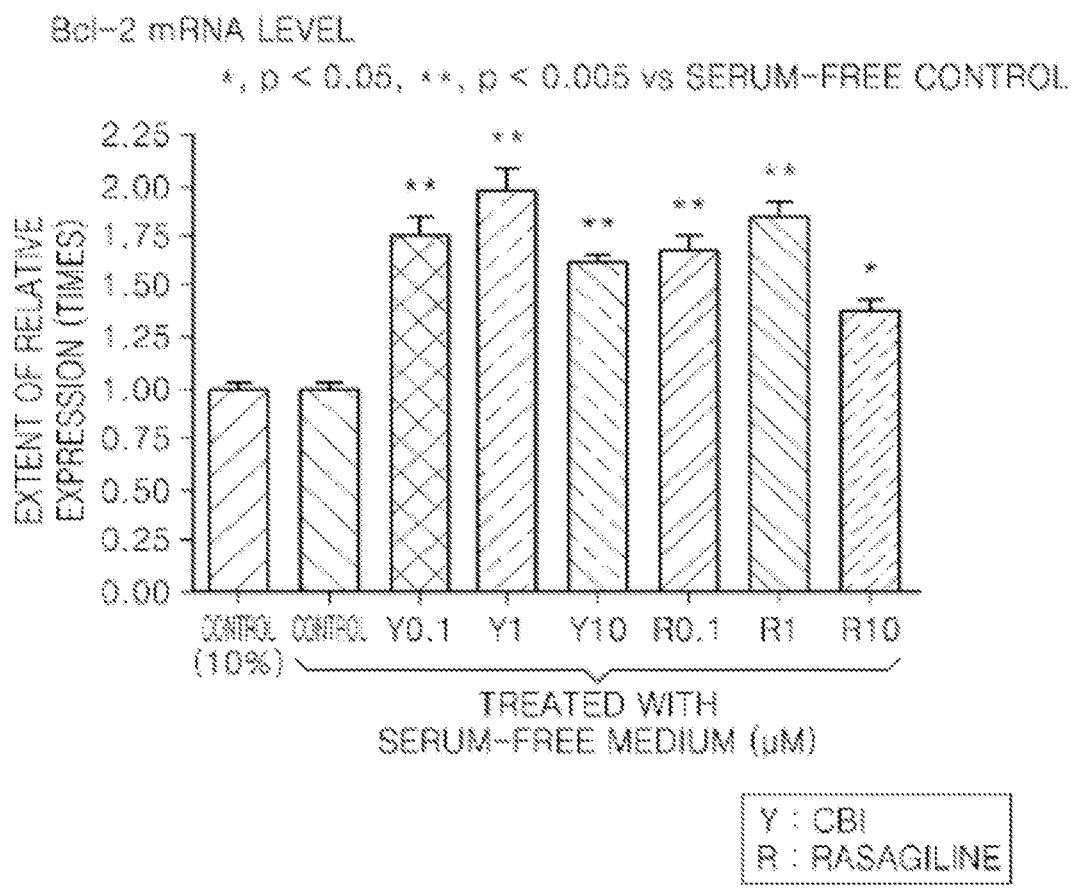
FIG. 10 is a graph showing measurement results of the amount of mRNA of Bcl-2 in MAO-B-deficient SH-SY5Y cells treated with CBI, according to an embodiment of the present invention.
Figure 11:
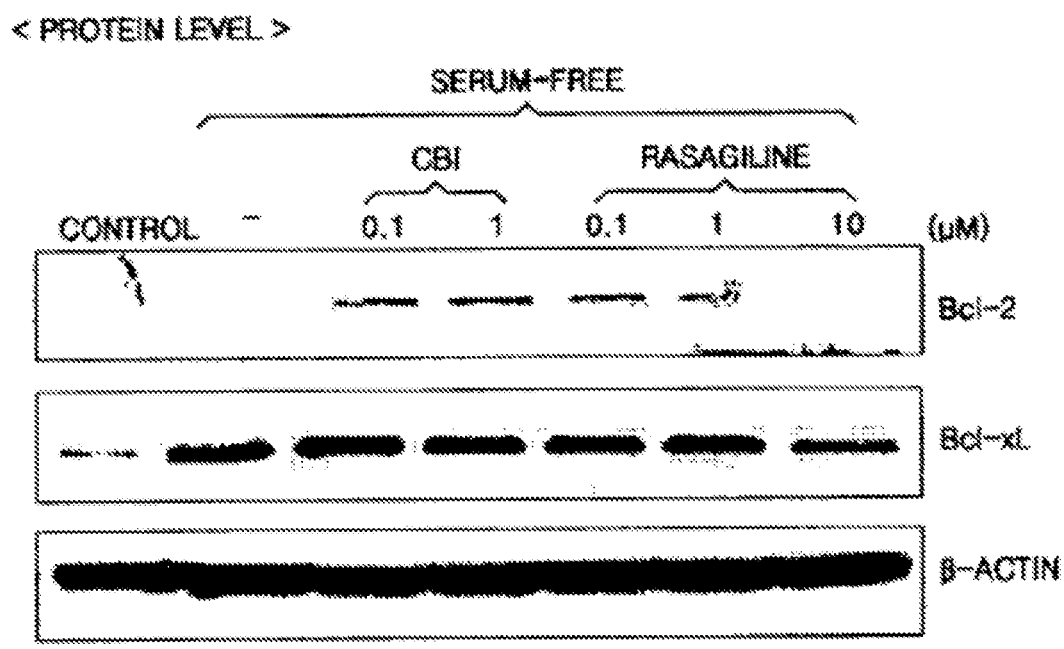
FIG. 11 illustrates images showing measurement results of the amounts of Bcl-2 and Bcl-xL proteins in MAO-B-deficient SH-SY5Y cells treated with CBI, according to an embodiment of the present invention.

As shown in FIGS. 10 and 11, it was confirmed that in the case of the apoptosis-induced neuron administered with CBI, the amount of mRNA of the Bcl-2 protein having an anti-apoptosis function was 1.5 to 2 times larger than that in the control, and the amount of the Bcl-2 protein was also 1.5 to 2 times larger than that in the control. In addition, it was confirmed that the amount of Bcl-xL, which is the other anti-apoptosis protein, was also larger than that in the control. From the results, it was confirmed that CBI had an effect of inhibiting apoptosis of neurons, and thus had a neuroprotective effect.

EXAMPLE 7

Confirmation of Neuroprotective Effect of CBI by Inducing the Expression of Neurotrophic Factor A neurotrophic factor is a protein that plays a crucial role in development, regeneration and repair of neurons, and examples of the neurotrophic factor include a brain-derived neurotrophic factor (BDNF), a glial cell line-derived neurotrophic factor (GDNF), and a nerve growth factor (NGF). The induction of the neurotrophic factor enables the inhibition of the apoptosis of neurons (*Nature medicine,* 15:331-337 (2009); *Brain Research Bulletin,* 57:817-822 (2002); *The Journal of Neuroscience,* 21:8108-8118 (2001); *The Journal of Pharmacology and Experimental Therapeutics,* 322:59-69 (2007); *TRENDS in Pharmacological Sciences,* 27:619-625 (2006)).

By using the same method as in Example 6, 0.1, 1 and 10 of CBI or 0.1, 1 and 10 of rasagiline were respectively added to apoptosis-induced cells, the resulting cells were further incubated in 5% of $CO_2$ at 37° C. for 24 hours, mRNA was extracted from the cultured cells, and thus the amounts of mRNA of BDNF, GDNF and NGF were measured by real-time RT-PCR.

Figure 12:
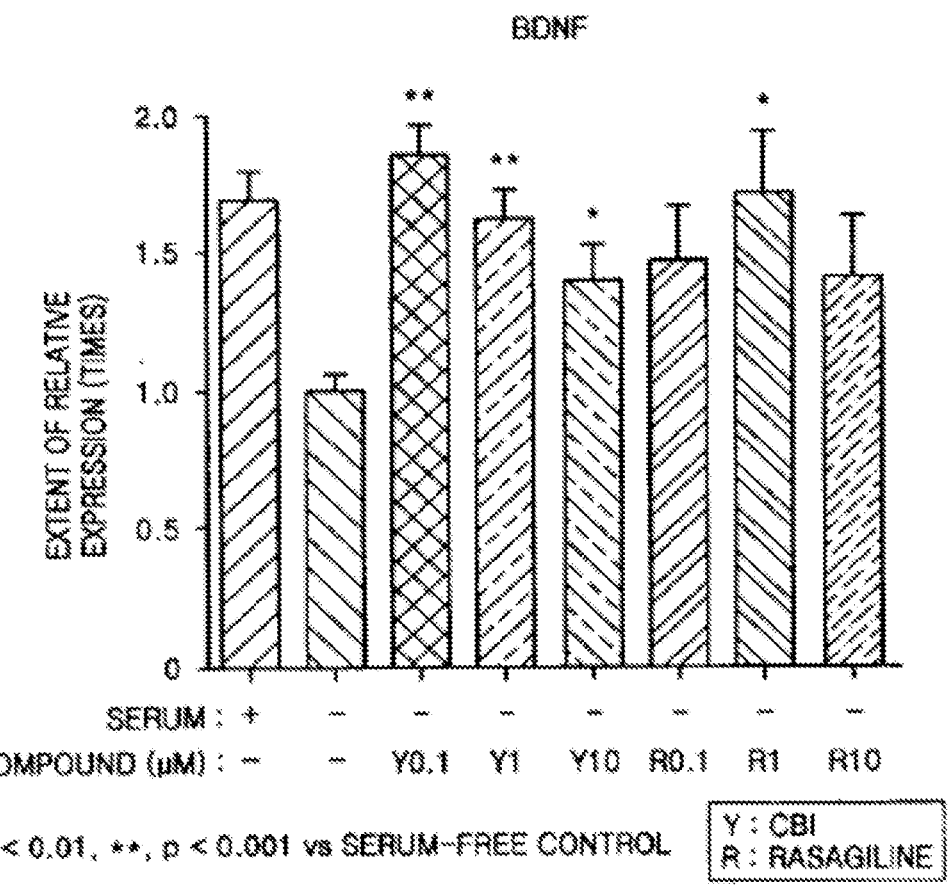
FIG. 12 is a graph showing measurement results of the amount of mRNA of BDNF in MAO-B-deficient SH-SY5Y cells treated with CBI, according to an embodiment of the present invention.
Figure 13:
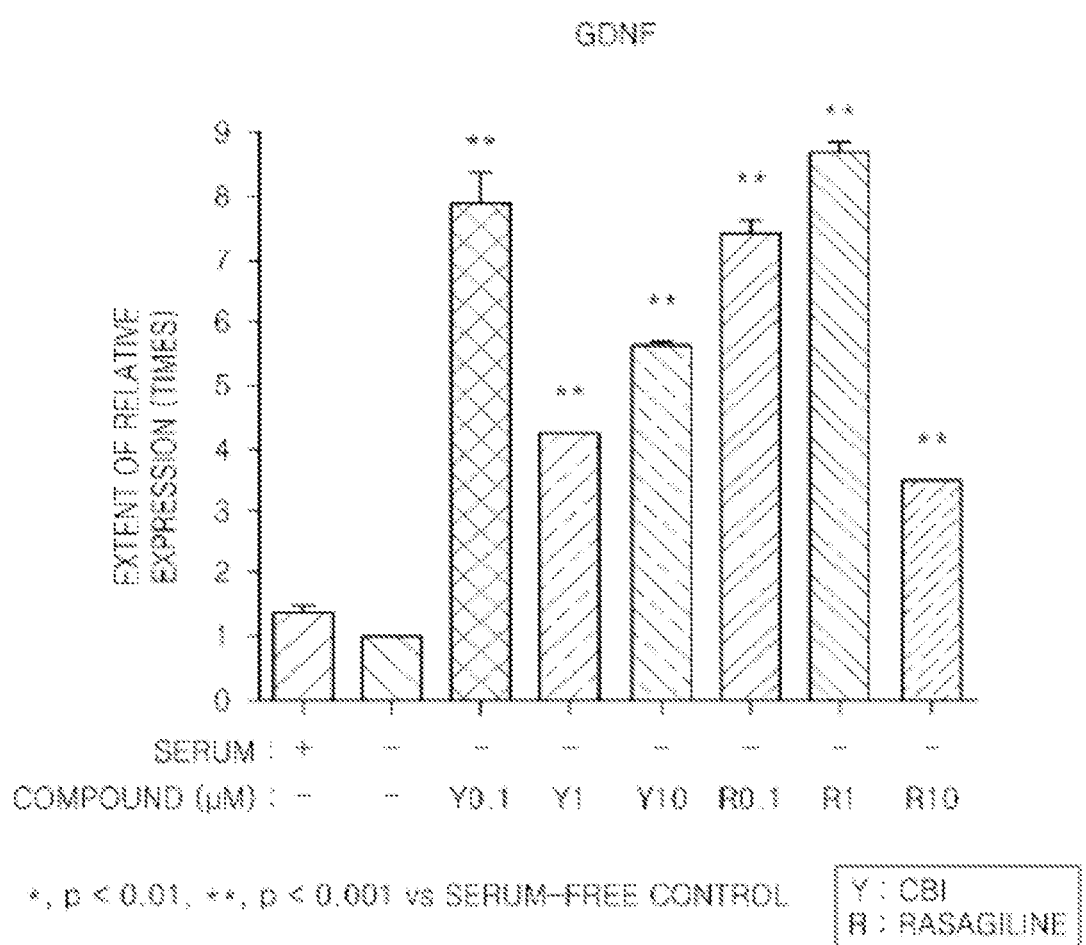
FIG. 13 is a graph showing measurement results of the amount of mRNA of GDNF in MAO-B-deficient SH-SY5Y cells treated with CBI, according to an embodiment of the present invention.
Figure 14:
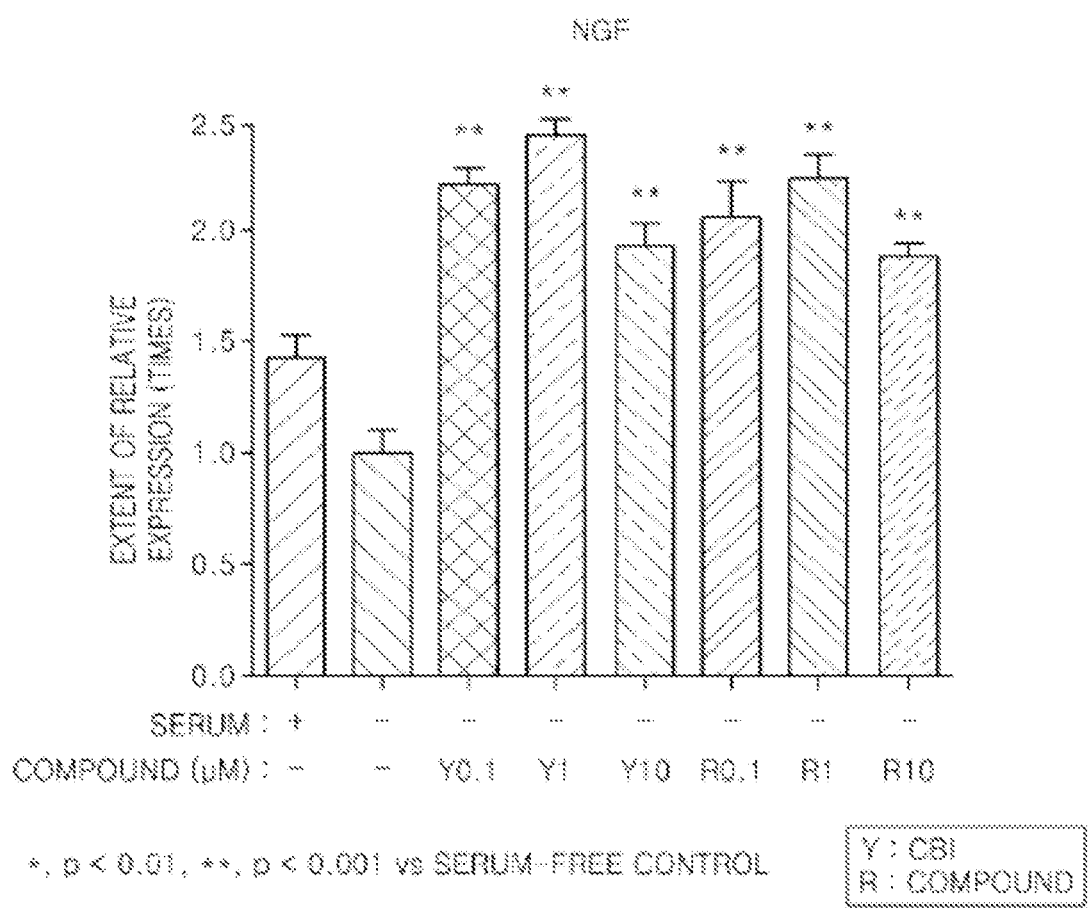
FIG. 14 is a graph showing measurement results of the amount of mRNA of NGF in MAO-B-deficient SH-SY5Y cells treated with CBI, according to an embodiment of the present invention.

As shown in FIGS. 12 through 14, it was confirmed that in the case of the apoptosis-induced neuron treated with CBI, the amounts of mRNA of BDNF, GDNF and NGF were respectively 1.5 to 2 times, 4 to 8 times and 2 to 2.5 times larger than in the control.

In addition, to confirm in vivo whether or not the neurotrophic factor was induced by the treatment of CBI, C57BL/6 mice (n=12, 8-week-old male, ORIENT BIO INC.) were used. The mice were divided into three groups (n=4 for each group), and an excipient (control), 1 mg/kg of CBI, and 1 mg/kg of rasagiline were respectively administered orally to the three groups without treatment of a neurotoxin once a day for 8 days. Next day after the last day of administration, striatum and substantia nigra tissues were taken out of each group of mice. mRNA was extracted from the cell of the taken tissue, and thus the amount of mRNA of NGF was measured by real-time RT-PCR.

Figure 15:
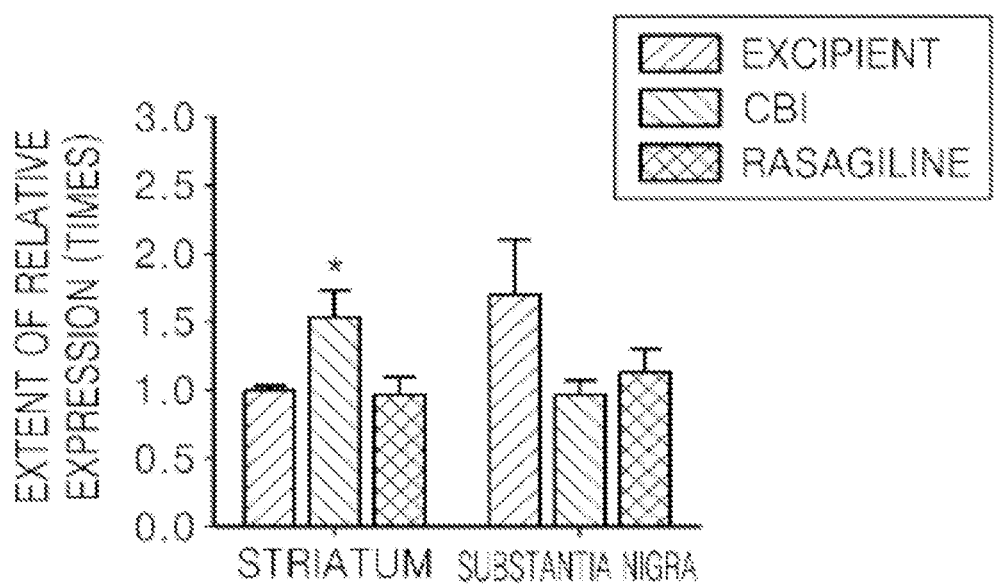
FIG. 15 is a graph showing measurement results of the amount of mRNA of NGF in a mouse administered with CBI, according to an embodiment of the present invention.

As shown in FIG. 15, it was confirmed that in the case of the group of mice treated with CBL the amount of mRNA of NGF in the striatum was about 1.7 to 2.5 times larger than that in the other groups of mice. In particular, it was confirmed that in the case of the group of mice treated with CBI, the expression of NGF in the striatum was significantly higher than that in the group of mice treated with rasagiline. The results indicate that CBI induces the expression of the neurotrophic factors of neurons, thereby being capable of inhibiting the apoptosis of neurons.

EXAMPLE 8

Figure 16:
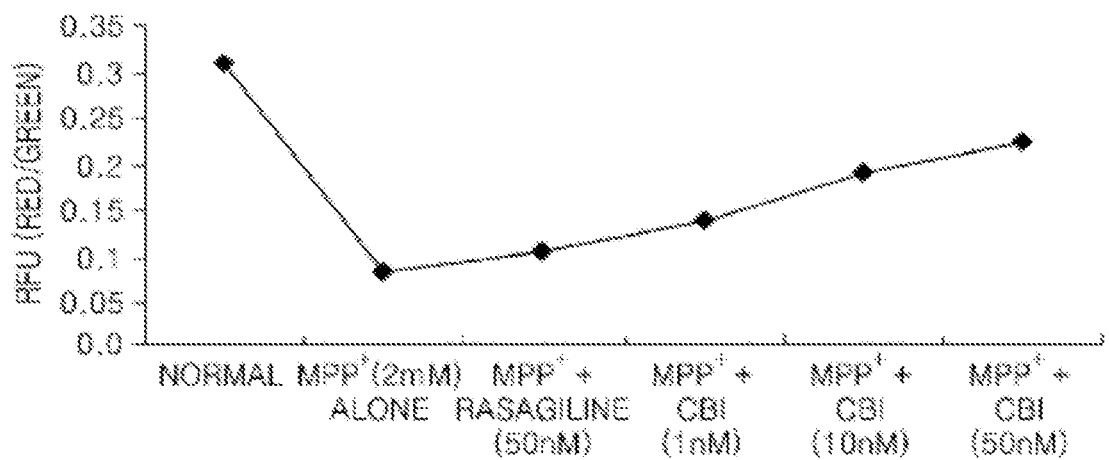
FIG. 16 is a graph showing membrane potential of mitochondria in MAO-B-deficient SH-SY5Y cells treated with CBT and MPP$^+$, according to an embodiment of the present invention.

Confirmation of Neuroprotective Effect of CBI by Improving Functions of Mitochondria in Neurons In this embodiment, MAO-B-deficient human neuroblastoma SH-SY5Y cells (Korean Cell Line Bank) were used. The cells were incubated in a DMEM medium in 5% of $CO_2$ at 37° C. for 24 hours. The cultured cells were divided into five groups, 2 mM of 1-methyl-4-phenyl-pyridium ($MPP^+$) was added to each group, three of the five groups were respectively treated with 1 nM, 10 nM and 50 nM of CBI, one of the other two groups was treated with 10 nM of rasagiline, and the CBI- or rasagiline-treated four groups were further incubated in 5% of $CO_2$ at 37° C. for 24 hours. The group with only $MPP^+$ added thereto was incubated under the same conditions as describe dabove. Subsequently, according to manufacturer's protocols, the transmembrane potential of mitochondria was determined using MitoPT™ kit (Immunochemistry Technology). The transmembrane potential of mitochondria was confirmed using a fluorescent plate reader (Tecan, Austria). When the transmembrane potential of mitochondria is low, green fluorescence is displayed, on the other hand, when it is high, red fluorescence is displayed. Thus, RFU values (red fluorescence value/green fluorescence value) were determined from the results, and the results are shown in FIG. 16.

$MPP^+$ reduces the transmembrane potential of mitochondria, thereby inducing the instability of mitochondria membrane. Mitochondria membrane permeabilization is an essential process in apoptosis, and thus the stability of mitochondria membrane can become a mechanism of anti-apoptosis (*Brain Res. Rev.,* 29:1-25 (1999)). As shown in FIG. 16, it was confirmed that in the case of the neurons with $MPP^+$ added thereto, the transmembrane potential of mitochondria was stabilized concentration-dependently by the treatment of CBI, and the stability effect of the transmembrane potential of mitochondria was about no less than 2 times higher than that in the group of neurons treated with the same concentration of rasagiline as that of CBI.

As described above, many neurodegenerative diseases such as a stroke, brain injuries, spinal cord injuries, amyotrophic lateral sclerosis, Huntington's disease, Alzheimer's disease, and Parkinson's disease are characterized in apoptosis of neurons (*The New England Journal of Medicine,* 348: 1365 (2003)), and the apoptosis of neurons is caused by the induction of apoptosis pathways by several internal or external factors. In addition, the stability of mitochondria membrane is a mechanism of anti-apoptosis, and it is known that the apoptosis of neurons is inhibited by Bcl-2 or Bcl-xL protein, and mitochondria membrane is stabilized by the protein (*Biochem Biophys Res Commun.,* 304(3):433-435 (2003); *The New England Journal of Medicine,* 348(14): 1365-1375 (2003); *Brain Res Rev.,* 29(1):1-25 (1999); *Journal of Neurological Sciences,* 283:240-320 (2009)). Thus, the results indicate that CBI stabilizes the transmembrane potential of mitochondria, thereby being capable of preventing or treating the neurodegenerative diseases described above.

In addition, apoptosis is known to be caused by mechanisms of release of cytochrome c from mitochondria and activation of caspase 3 (*The New England journal of Medicine,* 348:1365-1375 (2003)). To confirm whether or not the stability of the transmembrane potential of mitochondria by the treatment of CBI is associated with anti-apoptosis of neurons, cell extracts were obtained from the groups of cells, and thus the amount of cytochrome c and the activity of caspase 3 in the cell cytoplasm were measured.

EXAMPLE 8-1

Measurement of the Release of Cytochrome c

SH-SY5Y cells were incubated under the same conditions as described in Example 7, and then washed with PBS. A protease inhibitor cocktail (Roche) and a phosphatase inhibitor cocktail (Roche) were added to a hypertonic buffer (20 mM HEPES, 10 mM KCl, 2 mM $MgCl_2$, 1 mM EDTA), and the SH-SY5Y cells were treated with 100 ul of the resulting solution and then suspended uniformly. The resultant was maintained on ice for 30 minutes, and then centrifuged at 12,000 rpm for 20 minutes. Subsequently, the same amount of the supernatant was loaded onto a SDS-PAGE gel followed by electrophoresis, the gel was transferred onto a nitrocellulose membrane, the membrane was blotted using cytochrome c (Santacruz, sc13156) diluted to 1:2000 by using a well-known method in the art, and the expression of cytochrome c was evaluated using ECL kit (Amersham Pharmacia).

Figure 17:
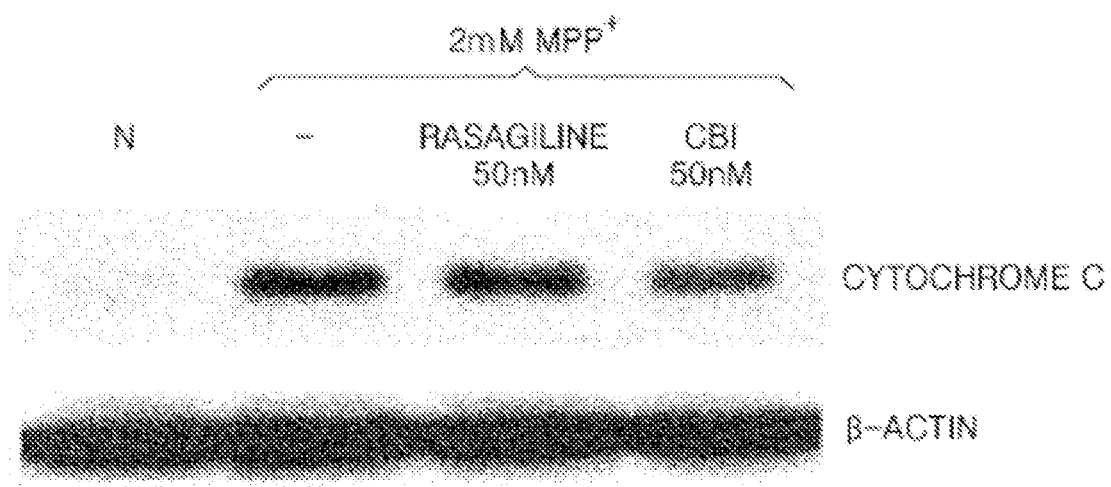
FIG. 17 illustrates images showing measurement results of the amount of cytoplasmic cytochrome c in MAO-B-deficient SH-SY5Y cells treated with CBI and MPP$^+$, according to an embodiment of the present invention.

As shown in FIG. 17, it was confirmed that in the case of the $MPP^+$-added neurons, the amount of cytochrome c in the cytoplasm was decreased by the treatment of CBI, and the amount of cytochrome c released from mitochondria was smaller than in the case of the $MPP^+$-added neurons treated with the same amount of rasagiline as that of CBI.

EXAMPLE 8-2

Measurement of the Activity of Caspase 3/7

Figure 18:
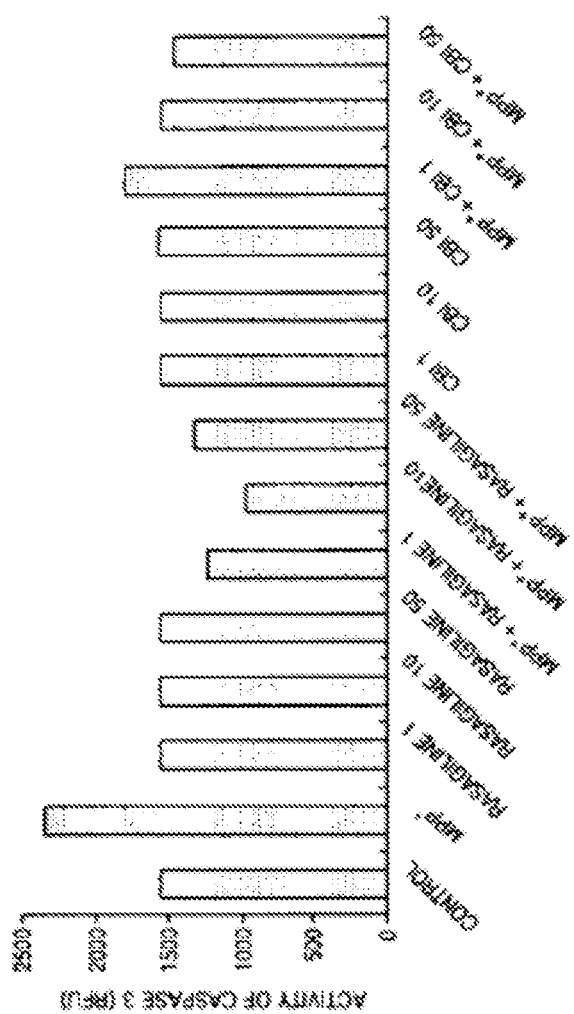
FIG. 18 is a graph showing measurement results of the activity of caspase-3 in MAO-B-deficient SH-SY5Y cells treated with CBI and MPP$^+$, according to an embodiment of the present invention.

SH-SY5Y cells were incubated in a 96-well plate at a concentration of $5 \times 10^5$ cells/well under the same conditions as described above, the cells were treated with 2 mM of $MPP^+$ and CBI (1, 5, 10 and 50 nM) or rasagiline (50 nM), and the resulting cells were incubated for 24 hours. Subsequently, 100 μl of Apo-ONE caspase 3/7 reagent (Promega, G7790) was added thereto and mixed therewith, and the resultant was further incubated for 4 hours. After the incubation was terminated, fluorescence was measured at an excitation wavelength of 495 nm and an emission wavelength of 521 nm by using a fluorescence plate reader (GeminiXPS, Molecular Devices). As shown in FIG. 18, it was confirmed that the activity of caspase 3 was reduced by the treatment of CBT, like in the case of the cells treated with rasagiline.

From the results of Example 8, it was confirmed that CBI stabilizes a mitochondria membrane in neurons, thereby preventing the release of cytochrome c from mitochondria, and reduces the activity of caspase 3 accordingly, thereby inhibiting the apoptosis of neurons.

As described above, many neurodegenerative diseases such as a stroke, brain injuries, spinal cord injuries, amyotrophic lateral sclerosis, Huntington's disease, Alzheimer's disease, and Parkinson's disease are characterized in apoptosis of neurons, and thus the results indicate that CBI inhibits the apoptosis of neurons, thereby being capable of preventing or treating the neurodegenerative diseases.

EXAMPLE 9

Confirmation of Neuroprotective Effect of CBI by Inhibiting Reactive Oxygen Species of Neurons In this embodiment, MAO-B-deficient human neuroblastoma SH-SY5Y cells (Korean Cell Line Bank) were used. The cells were cultured in a DMEM medium at 37° C. with 5% of $CO_2$ for 24 hours. The cultured cells were divided into three groups, 2 mM of $MPP^+$ was added to each group, one of the three groups was treated with 50 nM of CBI, one of the other two groups was treated with 50 nM of rasagiline, and the three groups were further incubated with 5% of $CO_2$ at 37° C. for 24 hours. The group with only $MPP^+$ added thereto was incubated under the same conditions as described above. Subsequently, the cells were stained with 2,7-dichlorofluorescein diacetate (DCF-DA), which is a fluorescence dye capable of detecting reactive oxygen species, and then observed using a confocal microscope (Nikon Co., Japan).

Figure 19:
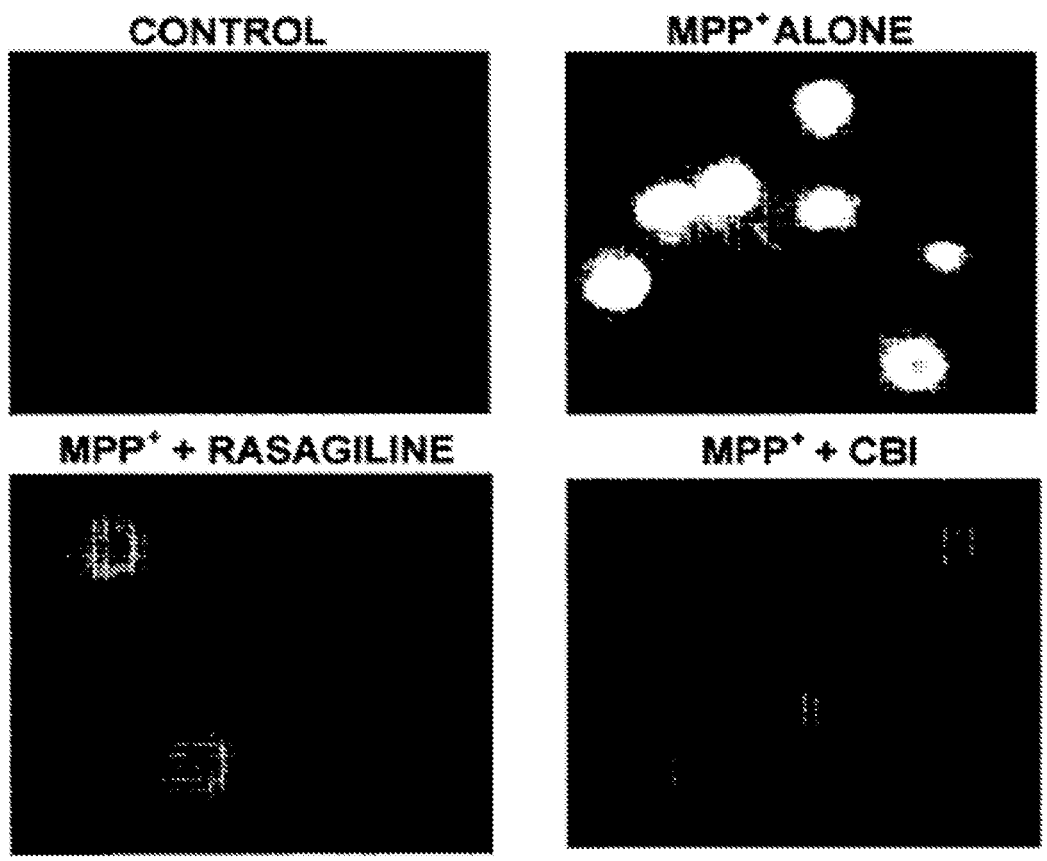
FIG. 19 illustrates microscopic images of reactive oxygen species in MAO-B-deficient SH-SY5Y cells treated with CBI and MPP$^+$, according to an embodiment of the present invention.
Figure 20:
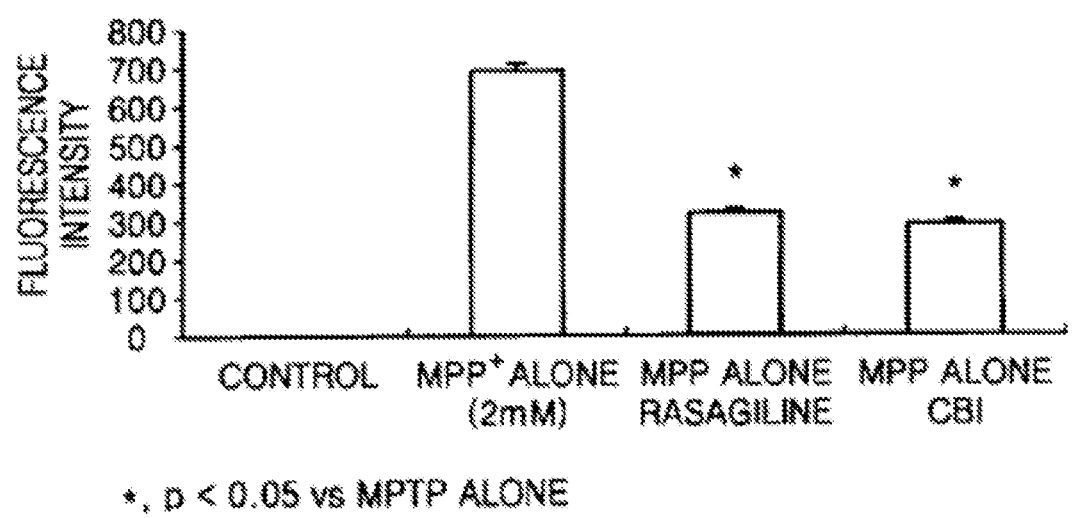
FIG. 20 is a graph showing that reactive oxygen species exist in MAO-B-deficient SH-SY5Y cells treated with CBI and MPP$^+$, according to an embodiment of the present invention.

As shown in FIGS. 19 and 20, in the case of the $MPP^+$-added neurons, reactive oxygen species were significantly decreased by the treatment of CBI, like in the case of the $MPP^+$-added neurons treated with the same concentration of rasagiline as that of CBI.

The generation of and an increase in reactive oxygen species in cells are known to induce apoptosis, and thus, from the results described above, it was confirmed that CBI induces a decrease in the reactive oxygen species, thereby inhibiting apoptosis. Such oxidative stress is known to cause various diseases related to apoptosis of neurons or neurodegeneration, for example, Alzheimer's disease, amyotrophic lateral sclerosis, demyelinating diseases, diabetic polyneuropathy, Down's syndrome, HIV neuropathy, Huntington's disease, multiple system atrophy, Parkinson's disease, stroke and ischemia-reperfusion injury, tauopathy, and traumatic brain damages (*Free radical Biology & Medicine,* 33(2):182-191 (2002)), and thus the results indicate that CBI induces a decrease in the reactive oxygen species, thereby inhibiting the oxidative stress, and prevents the apoptosis of neurons accordingly, and thus is used for prevention or treatment of the various neurodegenerative diseases.

EXAMPLE 10

Confirmation of Neuroprotective Effect of CBI by an Increase in Activity of Antioxidative Enzyme In this embodiment, MAO-B-deficient human neuroblastoma SH-SY5Y cells (Korean Cell Line Bank) were used. The SH-SY5Y cells were distributed into a 6-well plate at a concentration of $1.8 \times 10^5$ cells/well, and then incubated with 5% of $CO_2$ at 37° C. for 24 hours. The resulting cells were divided into three groups, 2 mM of $MPP^+$ was added to each group, two of the three groups were respectively treated 0.1, and the resultant was further incubated with 5% of $CO_2$ at 37° C. for 24 hours. The control group which was not treated with $MPP^+$ was incubated under the same conditions as described above. Subsequently, cell extracts were obtained from the cells, and thus the activities of antioxidative enzymes, i.e., catalase, superoxide dismutase (SOD) and glutathione peroxidase (GPx) were measured.

Figure 21:
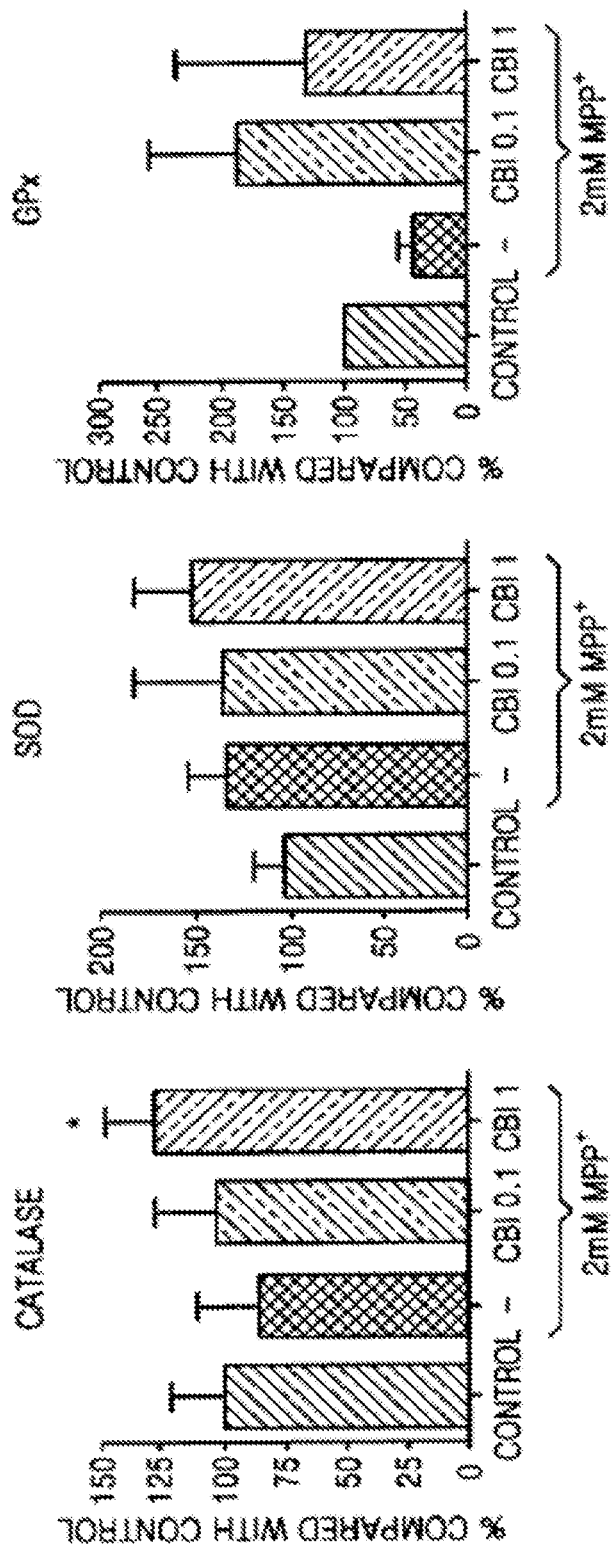
FIG. 21 illustrates graphs showing measurement results of the activities of catalase, superoxide dismutase (SOD) and glutathione peroxidase (GPx) in MAO-B-deficient SH-SY5Y cells treated with CBI and MPP$^+$, according to an embodiment of the present invention.

As shown in FIG. 21, the MPP+-added neurons exhibited a tendency of a decrease in the activities of catalase and GPx, compared with the group of cells that were not treated with MPP+, and the MPP+-added neurons treated with CBI exhibited an increase in a decreased activity of the antioxidative enzymes. In particularly, it was confirmed that the activity of the GPx in this group was about 2.5 to 4 times much higher than in the control.

In addition, to confirm in vivo whether the activities of the antioxidative enzymes were increased by the treatment of CBI, C57BL/6 mice (n=12), 8 to 9-week-old male) were used (ORIENT BIO INC.). The C57BL/6 mice were divided into three groups (n=4 for each group), and an excipient (control), 1 mg/kg of CBI and 1 mg/kg of rasagiline were respectively administered orally to the three groups without treatment of a neurotoxin for 8 days. Next day after the last day of administration, striatum and substantia nigra tissues were taken out of each group of mice. Cell extracts were obtained from the cells of the tissues, and thus the activities of the catalase, SOD and GPx were measured.

Figure 22:
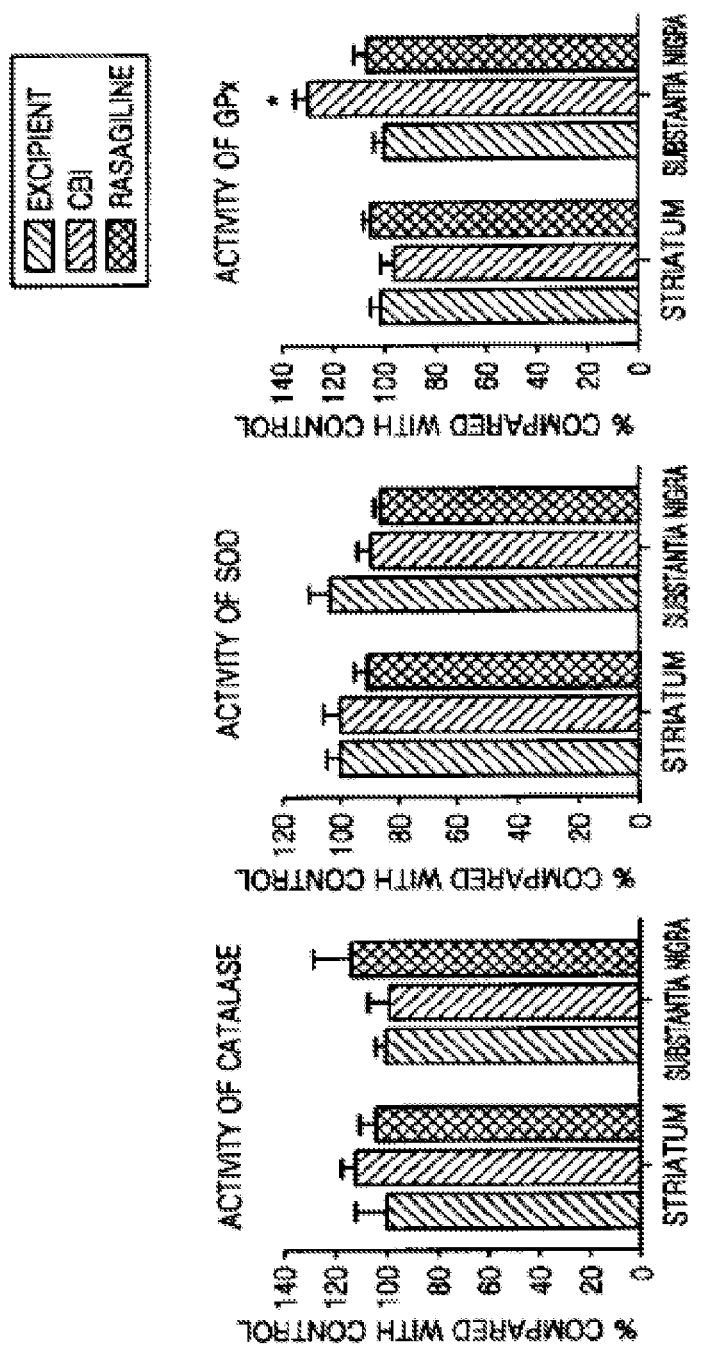
FIG. 22 illustrates graphs showing measurement results of the activities of catalase, SOD and GPx in striatum and substantia nigra of a mouse administered with CBI, according to an embodiment of the present invention.

As shown in FIG. 22, in the group of mice administered with CBI, there was no significant change in the activity of the SOD, however, the activity of the catalas was up by about 13% in the striatum and the activity of the GPx was up by about 28% in substantia nigra.

The generation of and an increase in reactive oxygen species in cells are known to induce apoptosis, and antioxidative enzymes are known to decompose the reactive oxygen species, and thus, from the results, it is confirmed that CBI increases the activity of antioxidative enzymes in neurons, in particular, the activity of GPx in substantia nigra, thereby inducing a decrease in reactive oxygen species, and is capable of inhibiting apoptosis, accordingly. In addition, the results indicate that CBI induces a decrease in reactive oxygen species, thereby inhibiting oxidative stress to prevent the apoptosis of neurons, and thus may be used for prevention or treatment of the various diseases described above.

EXAMPLE 11

Confirmation of Neurorestorative Effect of CBI

C57BL/6 mice (n=8/group (total 4 groups), 8-week-old; male) were used as an experimental model (substrain: C57BL/6NCrljBgi, available from ORIENT BIO INC.). 30 mg/kg of MPTP was administered to the mice via intraperitoneal injection once a day for 4 days. 4 days after the last day of administration, the mice were divided into three groups (n=4/group), and an excipient (control), 1 mg/kg of CBI and 1 mg/kg of rasagiline were respectively administered orally to the three groups once a day for 10 days. Next day after the last day of administration, striatum and substantia nigra tissues were taken out of each group of mice. To observe whether or not the number of neurites and spines per neuron in the tissues was increased, a coronal slice with a thickness of 200 um containing striatum or substantia nigra was prepared using a vibratome. Each group of mice was sacrificed, and the brain was taken out of each group and then placed in a cold, highly-concentrated sucrose dissection buffer bubbled with carbogen (5% $CO_2$ and 95% $O_2$) (87 mM NaCl, 2.5 mM KCl, 1.25 mM $NaH_2PO_4$, 25 mM $NaHCO_3$, 1 mM $CaCl_2$, 3 mM $MgCl_2$, 10 mM dextrose, and 75 mM sucrose). While the vibratome was performed, a slicing chamber was filled with the uniformly carbogenated sucrose dissection buffer. After the slicing process was terminated, all the slices were washed with PBS, and fixed with 4% paraformaldehyde in a PBS solution. The fixed brain slices were placed on a 1.5% agarose (in PBS) block. Images thereof were obtained using a confocal microscope (ZEISS LSM 510 META) by using Zeiss LSM image browser software (Carl Zeiss Microimaging, Germany, version 4.0 SP2).

Figure 23:
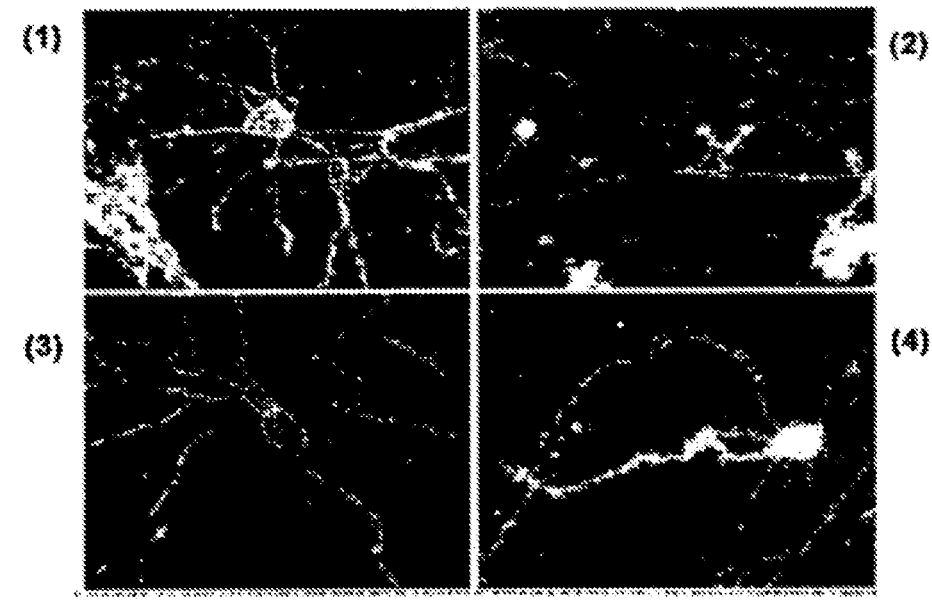
FIG. 23 illustrates microscopic images and an analysis graph showing whether or not neurite of a MPTP-induced mouse administered with CBI is recovered, according to an embodiment of the present invention.
Figure 23:
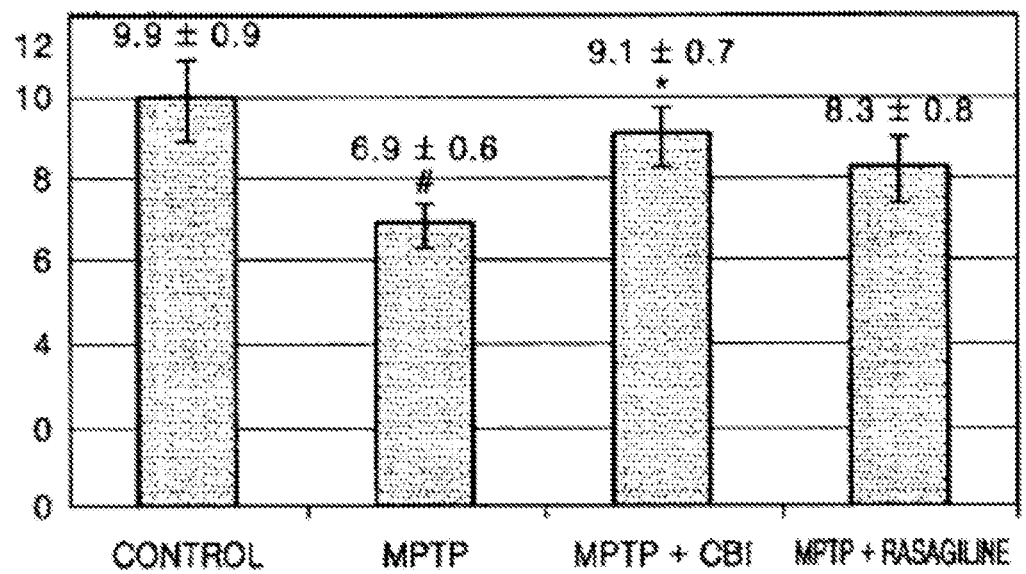
Figure 24:
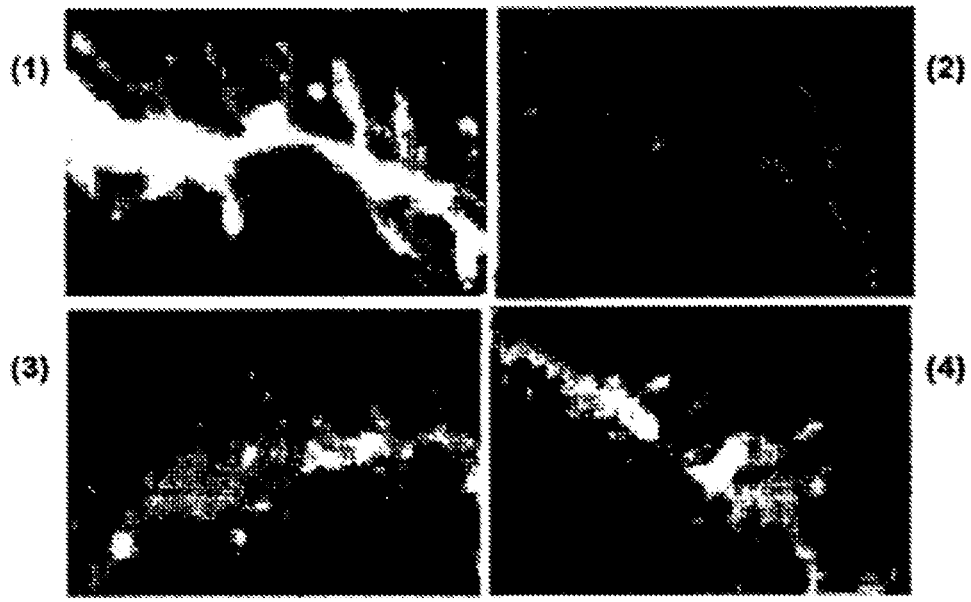
FIG. 24 illustrates microscopic images and an analysis graph showing whether or not spine of a MPTP-induced mouse administered with CBI is recovered, according to an embodiment of the present invention.
Figure 24:
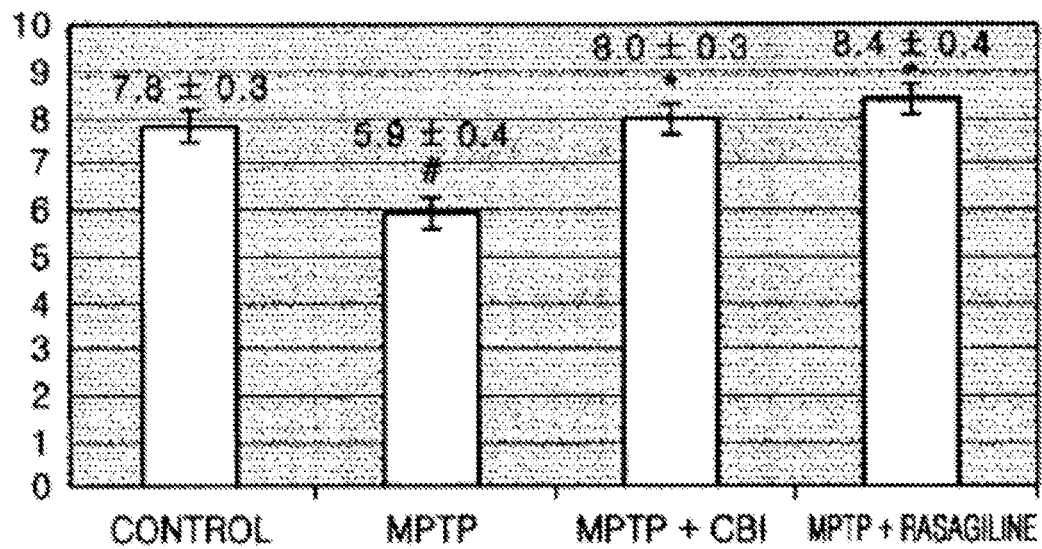

As shown in FIGS. 23 and 24, in the case of the group of MPTP-induced mice administered with CBI, the number of neurites increased, and the number of spines was also recovered to the level of normal cells. In particular, in the case of the group of MPTP-induced mice administered with rasagiline, an increase in the number of spines was observed, however, an increase in neurites did not exhibit statistical significance. From the results, it is confirmed that CBI inhibits apoptosis and also has an effect of enhancing neural plasticity.

EXAMPLE 12

Administration of CBI and Preparation of Tablet Containing CBI (Prediction)

The pharmaceutical composition according to the present invention is used in inhibiting apoptosis of neurons or neurodegeneration, or in neuroprotection or neurorestoration. A clinically suitable dose (oral administration) of the pharmaceutical composition is 25 mg~100 mg for an adult.

Based on the dose, a tablet containing components shown in Table 1 below was prepared using a general method. Avicel 102 (Microcrystalline cellulose) was used as an excipient.

TABLE 1

| Component | Amount |
| --- | --- |
| CBI | ~25 mg |
| Pobidon K30 | ~100 mg |
| Microcrystalline cellulose | ~100 mg |
| Sodium starch glycolate | ~7.5 mg |
| Magnesium stearate | ~2.5 mg |
| Total amount | ~235 mg |

A suitable dose of the components is 1 or 2 tablets containing the components per a day for an adult with a body weight of 60 kg.

According to one or more embodiments of the present invention, a pharmaceutical composition may effectively prevent or treat diseases related to apoptosis of neurons or neurodegeneration.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for treatment of a neurodegenerative disease, comprising:
    administering to a subject in need of such treatment a therapeutically effective amount of a compound of Formula I, a pharmaceutically acceptable salt, an isomer, a solvate, or a hydrate thereof, or any combination thereof:

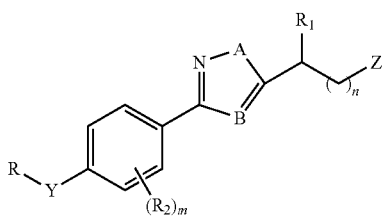

Formula I wherein R is selected from the group consisting of substituted or unsubstituted $C_1$-$C_{15}$ arylalkyl, substituted or unsubstituted $C_1$-$C_{15}$ heteroarylalkyl, and substituted or unsubstituted, linear, branched or cyclic $C_1$-$C_{10}$ alkyl;

Y is selected from the group consisting of O and —N—$R_1$;

$R_1$ is at least one selected from the group consisting of —H and linear or branched $C_1$-$C_3$ alkyl;

$R_2$ is selected from the group consisting of —H and halo;

A is selected from the group consisting of N, O, and S;

B is C or N;

Z is —OC(=O)$NH_2$;

m is an integer in the range of 0 to 4; and n is an integer in the range of 0 to 5.

2. The method of claim 1, wherein the compound of Formula 1 is selected from the group consisting of:

carbamic acid 3-(4-benzyloxy-phenyl)-isoxazole-5-yl methyl ester, carbamic acid 3-(4-benzyloxy-phenyl)-[1,2,4]oxadiazole-5-yl methyl ester, carbamic acid 3-(4-benzyloxy-phenyl)-isothiazole-5-yl methyl ester, carbamic acid 3-(4-benzyloxy-phenyl)-[1,2,4]thiadiazole-5-yl methyl ester, carbamic acid 3-(4-benzyloxy-2-chloro-phenyl)-isoxazole-5-yl methyl ester, carbamic acid 3-(4-benzyloxy-3-chloro-phenyl)-isoxazole-5-yl methyl ester, carbamic acid 3-(4-benzyloxy-3-bromo-phenyl)-isoxazole-5-yl methyl ester, carbamic acid 3-(4-benzyloxy-3-fluoro-phenyl)-isoxazole-5-yl methyl ester, carbamic acid 3-(4-benzyloxy-3,5-dimethyl-phenyl)-isoxazole-5-yl methyl ester, carbamic acid 3-[4-(1-phenyl-ethoxy)-phenyl]-isoxazole-5-yl methyl ester, carbamic acid 3-[4-(2-fluoro-benzyloxy)-phenyl]-isoxazole-5-yl methyl ester, carbamic acid 3-[4-(3-fluoro-benzyloxy)-phenyl]-isoxazole-5-yl methyl ester, carbamic acid 3-[4-(4-fluoro-benzyloxy)-phenyl]-isoxazole-5-yl methyl ester, carbamic acid 3-[4-(2,6-difluoro-benzyloxy)-phenyl]isoxazole-5-yl methyl ester, carbamic acid 3-[4-(2,3-difluoro-benzyloxy)-phenyl]-isoxazole-5-yl methyl ester, carbamic acid 3-[4-(3,5-difluoro-benzyloxy)-phenyl]-isoxazole-5-yl methyl ester, carbamic acid 3-[4-(3,4-difluoro-benzyloxy)-phenyl]-isoxazole-5-yl methyl ester, carbamic acid 3-[4-(2,4,6-trifluoro-benzyloxy)-phenyl]-isoxazole-5-yl methyl ester, carbamic acid 3-[4-(3-trifluoromethyl-benzyloxy)-phenyl]-isoxazole-5-yl methyl ester, carbamic acid 3-[4-(3-chloro-benzyloxy)-phenyl]-isoxazole-5-yl methyl ester, carbamic acid 3-[4-(2-chloro-benzyloxy)-phenyl]isoxazole-5-yl methyl ester, carbamic acid 3-[4-(4-chloro-benzyloxy)-phenyl]-isoxazole-5-yl methyl ester, carbamic acid 3-[4-(2,6-dichloro-benzyloxy)-phenyl]-isoxazole-5-yl methyl ester, carbamic acid 3-[4-(2,5-dichloro-benzyloxy)-phenyl]-isoxazole-5-yl methyl ester, carbamic acid 3-[4-(2-chloro-5-fluoro-benzyloxy)-phenyl]isoxazole-5-yl methyl ester, carbamic acid 3-[4-(3-nitro-benzyloxy)-phenyl]-isoxazole-5-yl methyl ester, 4-[4-(5-carbamoyloxymethyl-isoxazole-3-yl)-phenoxymethyl]-benzoic acid methyl ester, carbamic acid 3-[4-(4-methyl-benzyloxy)-phenyl]-isoxazole-5-yl methyl ester, carbamic acid 3-[4-(2-methyl-benzyloxy)-phenyl]-isoxazole-5-yl methyl ester, carbamic acid 3-[4-(3-methoxy-benzyloxy)-phenyl]-isoxazole-5-yl methyl ester, 3-[4-(3-trifluoromethyl-benzyloxy)-phenyl]-isoxazole-5-yl methyl ester, carbamic acid 3-[4-(4-isopropyl-benzyloxy)-phenyl]-isoxazole-5-yl methyl ester, and carbamic acid 3-[4-(4-tert-butyl-benzyloxy)-phenyl]-isoxazole-5-yl methyl ester.

3. The method of claim 1, wherein the compound of Formula I is a compound of Formula II is a compound of Formula II:

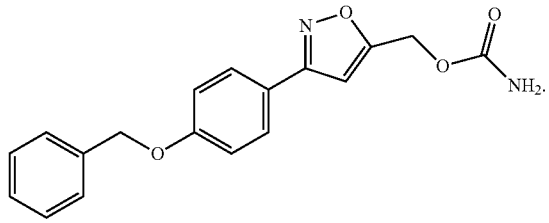

Formula II